(12) United States Patent
Wang et al.

(10) Patent No.: US 7,560,473 B2
(45) Date of Patent: Jul. 14, 2009

(54) AMINE DERIVATIVE WITH POTASSIUM CHANNEL REGULATORY FUNCTION, ITS PREPARATION AND USE

(75) Inventors: Hai Wang, Beijing (CN); Liuhong Yun, Beijing (CN); Huasong Feng, Beijing (CN); Fulin Li, Beijing (CN); Xingchun Tang, Beijing (CN); Huamei He, Beijing (CN); Rifang Yang, Beijing (CN); Wenyu Cui, Beijing (CN); Qixiu Gao, Beijing (CN); Gang Hu, Beijing (CN); Rusheng Zhao, Beijing (CN); Wei Liu, Beijing (CN); Chaoliang Long, Beijing (CN); Lin Wang, Beijing (CN); Xinqiang Lu, Beijing (CN); Lijun Liu, Beijing (CN); Yuan Yan, Beijing (CN)

(73) Assignee: Institute of Pharmacology and Toxicology Academy of Military Medical Sciences, P.L.A., Beijing (CN)

( * ) Notice: Subject to any disclaimer, the term of this patent is extended or adjusted under 35 U.S.C. 154(b) by 500 days.

(21) Appl. No.: 10/466,712

(22) PCT Filed: Jan. 21, 2002

(86) PCT No.: PCT/CN02/00029

§ 371 (c)(1),
(2), (4) Date: Aug. 12, 2004

(87) PCT Pub. No.: WO03/080556

PCT Pub. Date: Oct. 2, 2003

(65) Prior Publication Data

US 2004/0266822 A1    Dec. 30, 2004

(30) Foreign Application Priority Data

Jan. 19, 2001  (CN) ............................... 01 1 01655
Jan. 19, 2001  (CN) ............................... 01 1 01656

(51) Int. Cl.
  *A61K 31/44*    (2006.01)
  *A61K 31/405*   (2006.01)
  *C07C 211/00*   (2006.01)
  *C07D 211/70*   (2006.01)
  *C07D 209/18*   (2006.01)

(52) U.S. Cl. ................ 514/355; 514/415; 514/663; 564/463; 564/509; 564/307; 564/502; 546/316; 548/495

(58) Field of Classification Search ........ 564/305, 564/463, 307, 509, 502; 514/646, 663, 355, 514/415; 546/316; 548/495
See application file for complete search history.

(56) References Cited

U.S. PATENT DOCUMENTS 3,067,101 A    12/1962  Easton et al.
3,152,180 A    10/1964  Haaf
3,168,567 A     2/1965  Easton et al.

FOREIGN PATENT DOCUMENTS

| DE | 1197091 A | 7/1965 |
|---|---|---|
| GB | 873780 A | 7/1961 |
| GB | 1574477 | 9/1980 |
| JP | 4836129 | 5/1973 |
| JP | 3204855 | 9/1991 |
| WO | WO9522327 | 8/1995 |
| WO | WO0037474 | 6/2000 |

OTHER PUBLICATIONS

Hcaplus 79:42128.*
Hcaplus 61:40017.*
Hcaplus 117:7420.*
STN International, File CA, CA Full-text, Document No. 114:62158, Brown, Herbert C. et al: Chiral synthesis via organoboranes, 28. Reaction of a-chiral organyl dichloro-boranes with organyl azides providing a synthesis of secondary amines with exceptionally high enantiomeric purities, Journal of Organic Chemistry (1991), 56(3), 1170-5 (See whole document).
STN International, File CA, CA Full-text, Document No. 96:210106, Golovnya, R.V. et al: "Calculation of the gas-chromatographic retention indexes of secondary aliphatic amines from structural fragments", Zhurnal Analiticheskoi Khimii (1982). 37(2). 294-300 (See the whole document).
JP 50-013321A (Chemishe Werke Albert) Feb. 12, 1975 (See whole document).
Kharkevich D.A., "Ganglioblocking Properties of Branched Aliphatic Amines", Kurarepodobnye Ganglioblockiruyushchie Stredstava, 1970, pp. 247-252, Meditsina, Moscow, USSR.
Kharkevich, D.A., Ganglion-blocking Activity of Secondary and Tertiary Aliphatic and Alicyclic Amines, Farmakol. I Toksikol., 1962, 25, pp. 151-160.

(Continued)

*Primary Examiner*—Janet L Andres
*Assistant Examiner*—Binta M Robinson
(74) *Attorney, Agent, or Firm*—Cook Alex Ltd.

(57) ABSTRACT

The present invention provides amine derivatives represented by formula I, its isomers, racemes or optical isomers, pharmaceutical salts thereof, its amides or esters, pharmaceutical compositions containing said compounds and the preparation methods thereof. The invention also relates to the use of the above mentioned compounds in the preparation of drugs for the prophylaxis or treatment of cardiovascular diseases, diabetes, bronchial and urinary smooth muscle spasm as well as ischemic and anoxic nerve injury. The above compounds can be used to treat hypertension, angina diaphragmatic, myocardial infarction, congestive heart failure, arrhythmia, diabetes, spasmodic bronchial diseases, spasmodic bladder or ureter diseases, and depression.

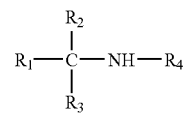

I

9 Claims, 8 Drawing Sheets

OTHER PUBLICATIONS

Madronero, Ramon, "Synthesis and Study of New Ganglioplegic Agents", An. Real Acad. Farm, 1968, 34(2), 173-95.

Hiltmann, R. et al., "Simple Aliphatic Amines with Ganglioplegic and Hypotensive Activity" Angew. Chemical. 1960, 72, 1001.

Bobranski Boguslaw et al., Aliphatic and Alicyclic Amines with Hypotensive Activity, Arch. Immunol, Therap. Exptl., 1962, 10(4), 905-924.

Stone Clement A., et al., "Chemistry and Structure-Activity Relationships of Mecamylamine and Derivatives", J. Med. Pharm. Chemical 1962, 5, 655-690.

Huet Jean, "Addition of Organolithums to Substituted Imines. III. Addition of Organolithium with Functional Groups to Aldimines", Bulletin Society Chim. France, 1964, 5, 967-972.

Volf Jiri et al., Hydrogenative Amination of Aliphatic and Alicyclic Ketones With Primary Amines with the Use of Palladium Catalyst, Sb. Vys. Sk. Chemical-Technol. Praze, Organic Chemical Technol., 1973, C19, 27-34.

Huet Jean, Addition of Organolithums to Substituted Imines. II. Addition of Organolithium to Various Compounds Containing a CN Group, Bulletin Society Chim. France, 1964, 5, 960-967.

Hennion G. F. et al., "Sterically Crowded Amines. IV. Secondary and Tertiary Bispropargylic Amines and their Hydrogenation Products", J. Organic Chemical, 1965, 30(8), 2645-2650.

International Preliminary Examination Report PCT/CN02/00029 pp. 1-4.

Ogawa, Masao et al: "2-Phenylisopropylamines" XP002372698; STN Database accession No. 79:42128 May 28, 1973 (May 28, 1973) Chemical Abstracts Service, Columbus Ohio.

Takematsu, Tetsuo et al Ogawa, Masao et al: "Addition of organolithiums to substituted imines. III. Addition of organolithiums with functional groups to aldimines Benzenesulfonamide derivatives 2-Phenylisopropylamines Addition of organolithiums to to substituted imines. II. Addition of organolithiums to various compounds containing a CN group" XP0023782699 retrieved from STN Database accession No. 61:40021 & Bull Soc Chim Fr, vol. 5, 1964, pp. 967-972.

Huet, Jean, Addition of organolithiums to substituted imines III. Addition of organolithiums with functional groups to aldimines. 1964. STN Document No. 61:40021, Chemical Abstracts Service, Columbus Ohio.

Madronero, Ramon, Synthesis and study of new ganglioplegic agents. 1968. STN Document No. 70:105857 Chemical Abstracts Service, Columbus Ohio.

Volf, Jiri, Hydrogenative amination of aliphatic and alicyclic ketones with with primary amines with the use of palladium catalyst. 1973. STN Document No. 70:105857 Chemical Abstracts Service, Columbus Ohio.

Ogawa, Masao, 2-phenylisopropylamines, 1971, STN Document No. 79:42128 Chemical Abstracts Service, Columbus Ohio.

Takematsu, Tetsuo, Benzenesulfomamide Derivatives, 1977. STN Document No. 89:72793 Chemical Abstracts Service, Columbus Ohio.

Huet, Jean, Addition of organolithiums to substituted imines II. Addition of organolithiums to various compounds having a CH group. 1964. STN Document No. 61:40020 Chemical Abstracts Service, Columbus Ohio.

Kharkevich, D. Ganglioblocking properties of branched aliphatic amines. 1971. STN Document No. 75:47363 Chemical Abstracts Service, Columbus Ohio.

Bobranski et al. Aliphatic and alicyclic amines with hypotensive activity. 1962. STN Document No. 59:85056, Chemical Abstracts Service, Columbus Ohio.

* cited by examiner

Fig.1 interaction of P1075, pinacidil, compound1 and glibenclamide with the binding sites in rat aortic strips labeled by [3H]P1075. The data shown were the means from 4 separate determinations.

Fig.2. Antagonism of glibenclamide against the activation of potassium currents by compound 1 in smooth muscle cells derived from rat intrapulmonary arteries. ( $\overline{X}$ ± SD; control, $n = 5$; compound1 10 μmol · L$^{-1}$, $n = 5$; compound 1 10 μmol · L$^{-1}$+ glybenclimade 30 μmol · L$^{-1}$ ,$n = 7$, $t$ -Test: * $p<0.05$,** $p<0.01$ vs control)

Fig3. Effects of repeated administration with compound1 for 7 days on degeneration of CA1 pyramidal neurons in dorsal hippocampus of jirds with global cerebral ischemia.
A: sham-operated jirds; B: ischemic jirds; ischemic jirds with compound1 at the doses of 0.5(C), 1.0(D), 2.0(E) and 4.0(F) mg/kg ip. (×600, hematoxylin eosin staining)

Fig4. Effects of repeated administration with compound1 for 7 days on TUNEL-staining of CA1 pyramidal neurons in dorsal hippocampus of jirds with global cerebral ischemia.

A: sham-operated jirds; B: ischemic jirds; ischemic jirds with compound1 at the doses of 0.5(C), 1.0(D), 2.0(E) and 4.0(F) mg/kg ip. (×600, TUNEL- staining)

Fig5. Effects of compound1 on the score of neurological deficits after onset of stroke in stroke-prone spontaneously hypertensive rats(SHRsp).

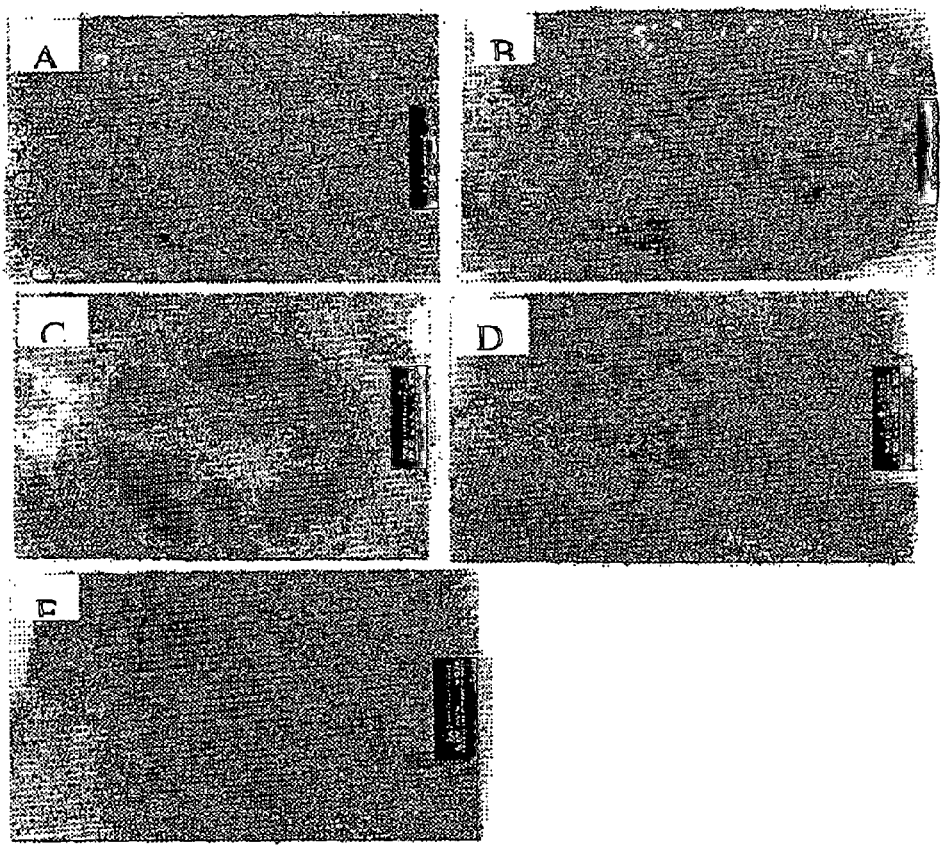

Fig.6

Fig 6. Ultrastructural features of cortical neuronal apoptosis induced by hypoxia-hypoglycemia and reoxygenation and effects of compound1 on apoptosis. A: Normal neurons, nuclear chromatin was evenly distributed; B: in low level oxygen and glucose treated groups, the cells showed chromatin condensation under the nuclear membrane; C: in low level oxygen and glucose treated groups, chromatin was condensed seriously; D: in low level oxygen and glucose treated groups, chromatin was fragmentation; E: in compound1 10μmol.L-1 treated group, chromatin had less condensed, cellular membrane kept integrity(×8800)

Fig.7 Effects of compound1 on apoptosis of primary cultured neurons derived from rat cortex. *$P<0.05$, **$P<0.01$ vs normal; #$P<0.05$, ##$P<0.01$ vs control.

AMINE DERIVATIVE WITH POTASSIUM CHANNEL REGULATORY FUNCTION, ITS PREPARATION AND USE

FIELD OF THE INVENTION

The present invention provides an amine derivative useful as a drug for the prophylaxis or treatment of cardiovascular diseases, diabetes, bronchial and urinary smooth muscle spasm, its stereoisomer, pharmaceutical salts, preparation methods thereof and pharmaceutical composition containing said compounds. The invention relates to the use of the above mentioned compounds as a drug for prophylaxis or treatment of cardiovascular diseases such as hypertension, arrhythmia, angina diaphragmatic, congestive heart failure and myocardial infarction, diabetes, bronchial and urinary smooth muscle spasm. The invention also relates to their uses as tool drugs for the investigation of the structure and functions of potassium channels, especially adenosine triphosphate (ATP)-sensitive potassium channels (i.e. $K_{ATP}$), in cardiovascular systems as well as neuronal and pancreatic cells. The present invention also encompasses the use of said compounds in the treatment of ischemic and anoxic nerve injury.

BACKGROUND OF THE INVENTION

Potassium channel is one of the important ion channels in mammalian, and has been revealed to be involved in maintaining the membrane potential of the excitable cells and the normal physiological functions of histiocytes. Compounds modulating the function of potassium channels can be used in the clinical practice for treating the commonly encountered and multiple cardiovascular diseases such as hypertension, angina diaphragmatic, arrhythmia, congestive heart failure and the like, diabetes, and diseases caused by smooth muscle spasm in bronchia, bladder and ureter.

Potassium channels are mainly classified into two groups: one is voltage-regulated potassium channel, the other is chemical-regulated potassium channel. Each group may be further divided into many subtypes. Using pharmacological methods to study the action properties of novel compounds plays very important roles in elucidating the pharmacological characteristics of potassium channels and their subtypes, as well as in searching for novel and highly effective drugs for clinical therapy.

$K_{ATP}$ is one of the chemical-regulated potassium channels. It distributes widely in cardiovascular systems, nerve and glands. Under pathological conditions such as ischemia or anoxia, $K_{ATP}$ mediates important pathological or physiological functions. It's an important target for the evaluation of the treatment of hypertension, angina diaphragmatic, arrhythmia, congestive heart failure, diabetes and some diseases caused by smooth muscle spasm in bronchi, bladder and ureter.

Drugs modulating potassium channels are termed as potassium channel openers (PCO) or potassium channel activators (KCA). They are classified into three types based on their physiological activities. Type-1 directly acts on transition sub-units independent of both ATP and nucleoside diphosphate (NDP), including pinacidil, levcromakalim, YM-934 and aprikalim, etc.; type-2 acts on sites which inhibit ATP binding or related sites thereof, and is dependent on ATP, including ER-001533, HOE234, etc.; type-3 acts on NDP binding sites and is dependent on NDP, such as nicorandil. Based on chemical structure, they may fall into the following groups: substituted cyanoguanidines or thioureas (e.g. pinacidil, ER-001533, U-94968, BRL-49074, etc.), substituted arylamides and derivatives thereof (e.g. nicorandil, KRN-239, Ki-1769, etc.), substituted benzopyranes and modifications thereof (e.g. levcromakalim, YM-934, Ro-31-6930, SDZ-PCO-400, UR8225, etc.), substituted cycloalkylthioformamides (e.g. aprikalim, etc.), substituted tertiary alcohols, dihydropyridines and their modifications, benzothiadiazines, pyrimidines and other heterocycles. Till now, there is no reports that secondary amines can modulate potassium channels. The antagonists of $K_{ATP}$ are sulfonylureas such as glyburide and gludipizide. They can antagonize the cardiovascular activities of KCAs. The major drawback of the reported KCAs is lack of tissue specificity and has severe side-effects such as reflex tachycardia, edema, cardialgia, flush and cardiomegalia, etc. Therefore, it is important to discover new medicament with higher tissue specificity.

PURPOSE OF THE INVENTION

The object of the present invention is to search for and develop new drugs for prophylaxis or treatment of cardiovascular diseases, especially for prophylaxis or treatment of the diseases related to the regulation of potassium channels.

BRIEF DESCRIPTION OF THE INVENTION

Through comprehensive and in-depth research, the inventors have discovered amine derivatives represented by formula I or formula $I_a$ which have potent activities of regulating potassium channels and can be useful in prophylaxis or treatment of cardiovascular diseases, diabetes, bronchial and urinary smooth muscle spasm. It is shown that the cardiovascular actitivities (e.g. affecting blood pressure, heart rate, cardiac contraction and dilation) of amine derivatives represented by formula I or formula $I_a$ can be antagonized by glyburide, an antagonist of $K_{ATP}$. Further studies suggested that the salts resulted from the combination of the amine derivatives included in the invention and inorganic acids or organic acids also have potent activities of regulating potassium channels and they have activities of selective antihypertension, reduction of oxygen consumption of the heart, vasodilation, and regulation of rhythm of the heart. The invention is based on these discoveries.

In one aspect, the invention relates to the use of an amine derivative represented by formula I,

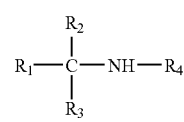

its isomer, raceme or optical isomer, pharmaceutical acid addition salts, amides or esters thereof in the preparation of the drugs useful for prophylaxis or treatment of cardiovascular diseases, diabetes, bronchial and urinary smooth muscle spasm. And the invention also relates to the uses of said compounds as the tool drugs for studying the structure and functions of potassium channels in cardiovascular system, neuronal and pancreatic cells, especially the potassium channels sensitive to adenosine triphosphate (ATP), i.e. $K_{ATP}$;

wherein $R_1$, $R_2$, and $R_3$ each independently represents hydrogen, saturated or unsaturated, linear or branched aliphatic $C_{1-20}$, $C_{3-20}$ cycloalkyl, substituted $C_{3-20}$ cycloalkyl, $C_{5-20}$ aryl, substituted $C_{5-20}$ aryl, $C_{5-20}$ heterocycloalkyl, substituted $C_{5-20}$ heterocycloalkyl, α-hydroxy $C_{2-20}$ alkyl, α-$C_{1-10}$ alkylcarboxy $C_{1-10}$ alkyl, α-$C_{6-14}$ arylcarboxy $C_{1-10}$ alkyl, α-substituted $C_{6-14}$ arylcarboxy $C_{1-10}$ alkyl, α-$C_{1-10}$ alkoxy $C_{1-10}$ alkyl, α-substituted $C_{5-10}$ aryloxy $C_{1-10}$ alkyl, α-amino $C_{1-20}$ alkyl, α-$C_{1-10}$ alkylamino $C_{1-10}$ alkyl, α-$C_{5-14}$ arylamino $C_{1-10}$ alkyl, α-substitued $C_{5-14}$ arylamino $C_{1-10}$ alkyl, α-$C_{1-10}$ alkylamido $C_{1-10}$ alkyl, α-$C_{6-14}$ arylamido $C_{1-10}$ alkyl, α-substituted $C_{6-14}$ arylamido $C_{1-10}$ alkyl;

$R_4$ represents hydrogen, saturated $C_{1-20}$ aliphatic alkyl, $C_{5-20}$ aryl, substituted $C_{5-20}$ aryl, $C_{3-20}$ heterocyclohydrocarbyl, substituted $C_{3-20}$ heterocyclohydrocarbyl, $C_{3-20}$ heterocyclo, substituted $C_{3-20}$ heterocyclo, linear $C_{1-20}$ fatty acyl, branched $C_{4-20}$ fatty acyl; or forms $C_{3-20}$ cyclohydrocarbyl or $C_{3-20}$ heterocyclo together with $R_1$, $R_2$ and $R_3$, wherein said heterocyclo represents single or fused heterocyclo composed of 1, 2 or 3 heteroatoms selected from nitrogen, oxygen or sulfur; The substituent of the above-mentioned groups is selecting from the group consisting of halogen, hydroxy, cyano, nitro, $C_{1-6}$ alkyl, $C_{1-6}$ alkoxy, $C_{1-6}$ alkylthio, $C_{1-6}$ alkyl substituted with one, two or three halogen, amino, $C_{1-10}$ hydrocarbylamino, $C_{1-10}$ hydrocarbylacyloxy, $C_{6-10}$ arylacyloxy, or $C_{1-10}$ amido.

In second aspect, the invention provides a new amine derivative represented by formula $I_a$, $$R'_2 - \underset{R'_3}{\overset{R'_1}{\underset{|}{\overset{|}{C}}}} - \underset{H}{\overset{}{N}} - R'_4 \quad I_a$$

its isomers, racemes or optical isomers, pharmaceutical acid addition salts, its amides or esters, which may be useful in prophylaxis or treatment of cardiovascular diseases, diabetes, bronchial and urinary smooth muscle spasm; wherein, (1) when $R'_1$ is isopropyl and each of $R'_2$ and $R'_3$ represents methyl, $R'_4$ may be isopropyl, n-butyl, isobutyl, t-butyl, cyclopropylmethyl, allyl, dimethylaminoethyl, diisopropylaminoethyl; or (2) when each of $R'_1$ and $R'_2$ represents methyl, $R'_3$—C—NH—$R'_4$ may be an amine derivative represented by the following formula $I'_a$, $$\underset{}{\overset{R}{\underset{|}{C}}} - \underset{H}{\overset{}{N}} - \underset{}{\overset{(CH_2)n}{\underset{|}{}}} R',\quad \text{formula I'a}$$

isomers, racemes or optical isomers thereof, wherein each of R and R' represents $C_{1-5}$ hydrocarbyl, n represents an integer of one to eight; or (3) when $R'_1$ represents phenyl, and $R'_2$ represents methyl, $R'_3$ may represent methyl, ethyl or isopropyl, and $R'_4$ may represent propyl or methoxycarbonyl methyl; or (4) when $R'_1$ represents $H_2NC(CH_3)_2$—, and each of $R'_2$ and $R'_3$ represents methyl, $R'_4$ represents isopropyl;

or when $R'_1$ represents $HOC(CH_3)_2$—, and each of $R'_2$ and $R'_3$ represents methyl, $R'_4$ represents $(CH_3)_2$ CH— or $(CH_3)_2$ CH($CH_3$)—;

or when $R'_1$ represents 1-hydroxycyclohexyl, and each of $R'_2$ and $R'_3$ represents methyl, or $R'_2$ and $R'_3$ together represent —$(CH_2)_4$— or —$(CH_2)_5$—, $R'_4$ represents $(CH_3)_2$ CH—;

or when $R'_1$ represents $(CH_3)_2C(ONO_2)$—, and each of $R'_2$ and $R'_3$ represents methyl, $R'_4$ represents $(CH_3)_2$ CH—;

or when $R'_1$ represents and each of $R'_2$ and $R'_3$ represents methyl, or $R'_2$ and $R'_3$ together represent —$(CH_2)_4$— or —$(CH_2)_5$—, $R'_4$ represents $(CH_3)_2$ CH—;

or when $R'_1$ represents and each of $R'_2$ and $R'_3$ represents methyl, or $R'_2$ and $R'_3$ together represent —$(CH_2)_4$— or —$(CH_2)_5$—, $R'_4$ represents $(CH_3)_2$ CH—;

or when $R'_1$ represents and each of $R'_2$ and $R'_3$ represents methyl, $R'_4$ represents $(CH_3)_2$ CH— or $(CH_3)_2$ CH($CH_3$)—;

or when $R'_1$ represents and each of $R'_2$ and $R'_3$ represents —$(CH_2)_5$—, $R'_4$ represents $(CH_3)_2$ CH($CH_3$)—; or (5) when $R'_1$ represents cyclohexyl, and each of $R'_2$ and $R'_3$ represents methyl, $R'_4$ may represent or when $R'_1$ represents cyclopentyl, and each of $R'_2$ and $R'_3$ represents —$(CH_2)_2$—, $R'_4$ may represent

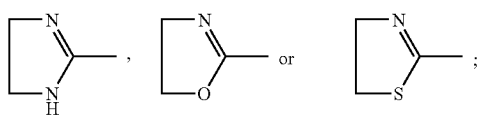

or when R'₁ represents isopropyl, and each of R'₂ and R'₃ represents methyl, R'₄ may represent

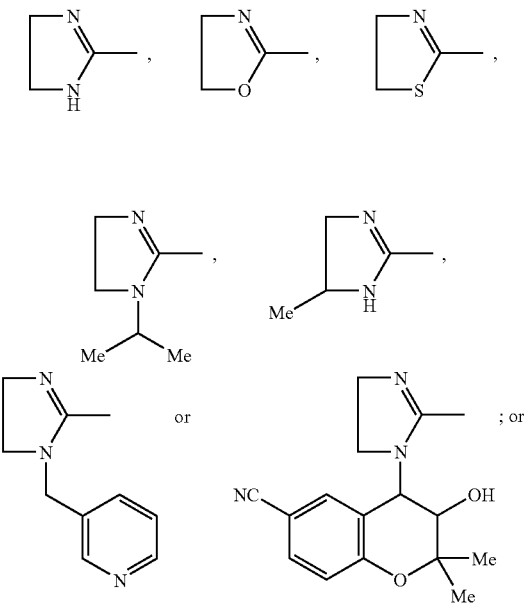

(6) when R'₁ represents isopropyl, and each of R'₂ and R'₃ represents methyl, R'₄ may represent Val-, Trp-, Ile-, Leu-, Phe-, O₂N-Arg-, Pro-, Leu-Val-, Trp-Trp-Trp- or (CH₃)₂CH—SO₂—; or R₄' may represent tosyl, nicotinyl, 4-chlorobenzoyl, morphorinoacetyl, 3-thienylacetyl, or 3-indolylacetyl; or when R'₁ represents cyclopropyl, and each of R'₂ and R'₃ represents —(CH₂)₂—, R'₄ represents Val-; or when R'₁ represents cyclohexyl, and each of R'₂ and R'₃ represents methyl, R'₄ represents Pro-; or when R'₁ represents cyclohexyl, and each of R'₂ and R'₃ represents —(CH₂)₂—, R'₄ represents Pro- or nicotinyl.

In third aspect, the invention relates to an amine derivative represented by formula I,

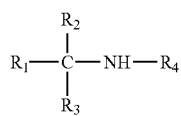

I its isomers, racemes or optical isomer, pharmaceutical acid addition salts, amides or esters, which are useful for prophylaxis or treatment of cardiovascular diseases, diabetes, bronchial and urinary smooth muscle spasm, wherein, R₁, R₂ and R₃ each independently represents hydrogen, saturated or unsaturated, linear or branched C$_{1-20}$ aliphatic group, C$_{3-20}$ cycloalkyl, substituted C$_{3-20}$ cycloalkyl, C$_{5-20}$ aryl, substituted C$_{5-20}$ aryl, C$_{5-20}$ heterocyclohydrocarbyl, substituted C$_{5-20}$ heterocyclohydrocarbyl, α-hydroxy C$_{2-20}$ alkyl, α-C$_{10}$ alkylcarboxy C$_{1-10}$ alkyl, α-C$_{6-14}$ arylcarboxy C$_{1-10}$ alkyl, α-substituted C$_{6-14}$ arylcarboxy C$_{1-10}$ alkyl, α-C$_{1-10}$ alkoxy C$_{1-10}$ alkyl, α-substituted C$_{5-10}$ aryloxy C$_{1-10}$ alkyl, α-amino C$_{1-20}$ alkyl, α-C$_{1-10}$ alkylamino C$_{1-10}$ alkyl, α-C$_{5-14}$ arylamino C$_{1-10}$ alkyl, α-substituted C$_{5-14}$ arylamino C$_{1-10}$ alkyl, α-C$_{1-10}$ alkylamido C$_{1-10}$ alkyl, α-C$_{6-14}$ arylamido C$_{1-10}$ alkyl, α-substituted C$_{6-14}$ arylamido C$_{1-10}$ alkyl;

R₄ represents hydrogen, saturated C$_{1-20}$ aliphatic alkyl, C$_{5-20}$ aryl, substituted C$_{5-20}$ aryl, C$_{3-20}$ heterocyclohydrocarbyl, substituted C$_{3-20}$ heterocyclohydrocarbyl, C$_{3-20}$ heterocyclo, substituted C$_{3-20}$ heterocyclo, linear C$_{1-20}$ fatty acyl, branched C$_{4-20}$ fatty acyl, or forms C$_{3-20}$ cyclohydrocarbyl or C$_{3-20}$ heterocyclo together with R₁, R₂ or R₃; wherein, said heterocyclo represents single or fused heterocyclo composed of 1, 2 or 3 heteroatoms of nitrogen, oxygen or sulfur; the substituent of the above-mentioned groups is selected from the group consisting of halogen, hydroxy, cyano, nitro, C$_{1-6}$ alkyl, C$_{1-6}$ alkoxy, C$_{1-6}$ alkylthio, C$_{1-6}$ alkyl substituted with one, two or three halogen, amino, C$_{10}$ hydrocarbylamino, C$_{1-10}$ hydrocarbylacyloxy, C$_{6-10}$ arylacyloxy, or C$_{1-10}$ amido.

In another aspect, the invention relates to a pharmaceutical composition which is composed of at least an amine derivative represented by formula I$_a$ or formula I, its isomers, racemes or optical isomers or its pharmaceutical acid addition salts, and pharmaceutical carriers or excipients.

The invention also relates to a new method for prophylaxis or treatment of cardiovascular diseases such as hypertension, arrhythmia, angina diaphragmatic, congestive heart failure and myocardial infarction, diabetes, bronchial and urinary smooth muscle spasm, which includes administering a therapeutically effective amount of an amine derivative represented by formula I$_a$ or formula I, isomers, racemes or optical isomer thereof to a patient suffered from a cardiovascular disease such as hypertension, arrhythmia, angina diaphragmatic, congestive heart failure or myocardial infarction, diabetes spasm of bronchial or urinary smooth muscles.

The invention also relates to a process for preparation of a compound represented by the above-mentioned formula I$_a$ which comprises dissolving a primary amine R'₁R'₂R'₃CNH₂ and R'₄X into an organic solvent and heating to 50-300 degree of centigrade and/or pressurizing to 0.1-20 million pascal, wherein R'₁, R'₂, R'₃ and R'₄ are defined as above, X represents a leaving group such as halogen and sulfonyloxy. The reaction is carried out in the presence of a catalyst which may be an acid absorbent and/or a phase tranfer catalyst, wherein the acid absorbent is a Lewis base including a tertiary amine or an inorganic base, and the phase transfer catalyst is glycol or polyglycol, wherein said organic solvent is toluene, xylene, 1,2-dichloroethane, 1,4-dioxane, dimethoxyethane, N,N-dimethylformide, N,N-dimethylacetamide, N-methylpyrrolidone, N,N-dimethylaniline or N,N-diethylaniline. The primary amine R'₁R'₂R'₃CNH₂ is prepared by hydrolysis of hydrocarbylurea R'₁R'₂R'₃CNHCONH₂, which is manufactured by reaction of urea with either an alkene or an alcohol of R₁' R₂' R₃'C or a mixture of both in the presence of concentrated sulfuric acid and a organic acid under 20-200 degree of centigrade, wherein said organic acid is selected from acetic acid, trifluoacetic acid or methanesulfonic acid.

The invention also provides another process for preparation of a compound represented by formula a, which comprises heating the mixture of the primary amine R'₁R'₂R'₃CNH₂ and the aldehyde or ketone of R'₄ to 30-300 degree of centigrade and/or pressurizing it to 0.1-20 million pascal in the presence or absence of an organic solvent, wherein R'₁, R'₂, R'₃ and R'₄ are defined as above, the organic solvent are excess amount of aldehyde or ketone of R'₄, toluene, xylene, 1,2-dichloroethane, 1,4-dioxane, dimethoxyethane, methanol or ethanol. The reaction is carried out in the presence of a catalyst such as palladium carbon, Raney nickel, platinic oxide and nickel-copper.

The invention also provides another process for preparation of a compound represented by formula $I_a$, which comprises reacting the enamine or Schiff base or nitrone of $R'_1R'_2CNHR'_4$ with an organometallic compound $R'_3M$; or reducing or catalytically hydrogenating the enamine or schiff base of $R_1' R_2' R_3'CNR_4'$, wherein M is selected from the group of lithium, sodium, magnesium, aluminium and zinc.

The above-mentioned process also includes steps of preparing the isomeric compounds or optical isomers of the above-mentioned product through asymmetrical reaction or resolution. The process also includes steps of preparing a pharmaceutically acceptable salt by the addition of the above-mentioned product to an inorganic or organic acid. Examples of the acid addition salts are salts with inorganic acids such as hydrochloric acid, sulfuric acid, phosphoric acid and hydrobromic acid, or salts with organic acids such as acetic acid, oxalic acid, citric acid, gluconic acid, succinic acid, tartaric acid, tosylic acid, methanesulfomic acid, benzoic acid, lactic acid and maleic acid.

DESCRIPTION OF THE DRAWINGS

FIG. 6 shows the effects of compound 1 on grade value of symptoms in nerve after cerebral apoplexy.

DETAIL DESCRIPTION OF THE INVENTION

Figure 1:
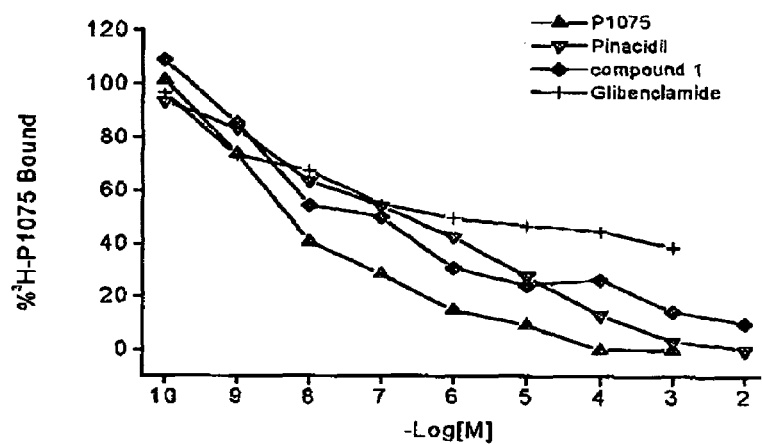
FIG. 1 shows the interaction of P1075, pinacidil, the compound in example 1 (referred as compund 1 hereinafter) and glibenclamide with the binding site in rat aortic strips labeled with [³H]P1075.

According to the present invention, the term of "cardiovascular diseases" in this invention refers to, for example hypertension, angina diaphragmatic, myocardial infarction, congestive heart failure, arrhythmiam, and so on.

According to the invention, the term "ischemic and anoxic nerve injury" caused by conditions such as cerebral apoplexy, transient ischemia attack, cerebral infarction, vertebro—basilar artery insufficiency, cerebral vasular dementia, hypertensive encephalopathy, cerebral edema, and cerebral trauma.

According to the present invention, for the compound represented by formula I, $R_1$ preferably represents tertiary butyl, cyclohexyl, cyclopentyl, cyclobutyl, cyclopropyl, isopentyl, isobutyl; or $R_1$ represents α-substituted cyclohexyl, cyclopentyl, cyclobuty, cyclo-propyl, isohexyl, isopentyl, isobutyl or isopropyl, wherein the above-mentioned substitutent may be amino, hydroxy, hydrocarbylamino of 1 to 10 carbons, hydrocarbyloxy of 1 to 6 carbons, hydrocarbylacyloxy of 1 to 10 carbons, arylacyloxy of 6 to 10 carbons and amido of 1 to 10 carbons;

$R_2$ or $R_3$ preferably represents hydrogen, chained carbohydron of 1 to 12 carbons or cyclic carbohydron of 3 to 8 carbons;

and $R_4$ preferably represents hydrogen, saturated aliphatic alkyl of 1 to 20 carbons, cycloalkyl of 3 to 20 carbons, acyl of 1 to 10 carbons, $C_{1-10}$ hydrocarbylamino $C_{1-10}$ alkyl, sulfoxidyl of 1-20 carbons, amino acid residues and lower molecule weight polypeptide thereof, β-nitrovinyl, β-cyanovinyl, substituted, carboimido, heterocyclo of 3-20 carbons and heterocycloacyl of 4-20 carbons.

According to the invention, for the compound represented by formula I, more preferably, each of $R_2$ and $R_3$ represents methyl, ethyl, propyl, or $R_2$ and $R_3$ represent propylene, butylene, pentylene and hexylene.

In one preferable enbodiment of the invention, the above-mentioned $R_1$ represents isopropyl, each of $R_2$ and $R_3$ represents methyl.

According to the invention, the compound represented by formula Ia may be selected from the group consisting of the following compounds:

N-(1-methylethyl)-2,3-dimethyl-2-butylamine;
N-propyl-2,3-dimethyl-2-butylamine;
N-(2-methylpropyl)-2,3-dimethyl-2-butylamine;
N-cyclopropylmethyl-2,3-dimethyl-2-butylamine;
N-allyl-2,3-dimethyl-2-butylamine;
N-{2-[di(1-methylethyl)amino]ethyl}-2,3-dimethyl-2-butylamine;
N-butyl-2,3-dimethyl-2-butylamine;
N-propyl-α-methylphenylpropylamine;
N-propyl-α,β-dimethyl-phenylpropylamine;
N-(3-pyridyl)formacyl-2,3-dimethyl-2-butylamine;
N-valyl-2,3-dimethyl-2-butylamine;
N-tryptophanyl-2,3-dimethyl-2-butylamine;
N-(N-nitro)arginyl-2,3-dimethyl-2-butylamine;
N-phenylalanyl-2,3-dimethyl-2-butylamine;
N-leucyl-2,3-dimethyl-2-butylamine;
N-isoleucyl-2,3-dimethyl-2-butylamine;
N-tosyl-2,3-dimethyl-2-butylamine;
N-(1-methylethyl)-2,3-dimethyl-3-hydroxy-2-butylamine;
N-cinnamoyl-N-(1-methylethyl)-2,3-dimethyl-2-butylamine;
N-(1-methylethyl)-N-(2,4,5-trichlorophenoxyacetyl)-2,3-dimeth yl-2-butylamine.

According to this invention the compound represented by formula I can be in the form of an acid addition salt. Examples of the acid addition salt are salts with inorganic acids such as hydrochloric acid, sulfuric acid, phosphoric acid, hydrobromic acid; and salts with organic acids such as acetic acid, oxalic acid, citric acid, gluconic acid, succinic acid, tartaric acid, tosylic acid, methanesulfonic acid, benzoic acid, lactic acid and maleic acid, for example, N-(1-methylethyl)-2,3-dimethyl-2-butylamine hydrochloride and N-(1-methylethyl)-2,3-dimethyl-2-butylamine tosylate.

The invention further relates to a new amine derivative represented by formula $I_a$,

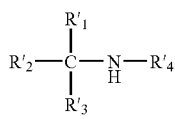

its isomers, racemes or optical isomers and pharmaceutical acid addition salts, which may be useful in prophylaxis or treatment of cardiovascular diseases, diabetes, bronchial and urinary smooth muscle spasm; wherein, (1) when $R'_1$ represents isopropyl and each of $R'_2$ and $R'_3$ represents methyl, $R'_4$ may be isopropyl, n-butyl, isobutyl, t-butyl, cyclopropylmethyl, allyl, dimethylaminoethyl, diisopropylaminoethyl; or (2) when each of $R'_1$ and $R'_2$ represents methyl, $R'_3$—C—NH—$R'_4$ may be an amine derivative represented by the following formula $I'_a$,

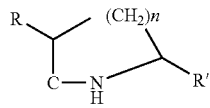

isomers, racemes or optical isomers thereof, wherein each of R and R' represents a hydrocarbyl group of one to five carbon atoms, n represents an integer of one to eight; or (3) when $R'_1$ represents phenyl, and $R'_2$ represents methyl, $R'_3$ represents methyl, ethyl or isopropyl, and $R'_4$ represents propyl or methoxycarbonyl methyl; or (4) when $R'_1$ represents $H_2NC(CH_3)_2$—, and each of $R'_2$ and $R'_3$ represents methyl, $R'_4$ represents isopropyl;

or when $R'_1$ represents $HOC(CH_3)_2$—, and each of $R'_2$ and $R'_3$ represents methyl, $R'_4$ represents $(CH_3)_2CH$— or $(CH_3)_2CH(CH_3)$—;

or when $R'_1$ represents 1-hydroxycyclohexyl, and each of $R'_2$ and $R'_3$ represents methyl, or $R'_2$ and $R'_3$ together represent —$(CH_2)_4$— or —$(CH_2)_5$—, $R'_4$ represents $(CH_3)_2CH$—;

or when $R'_1$ represents $(ONO_2)C(CH_3)_2$—, and each of $R'_2$ and $R'_3$ represents methyl, $R'_4$ represents $(CH_3)_2CH$—;

or when $R'_1$ represents

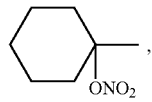

and each of $R'_2$ and $R'_3$ represents methyl, or $R'_2$ and $R'_3$ together represent —$(CH_2)_4$— or —$(CH_2)_5$—, $R'_4$ represents $(CH_3)_2CH$—;

or when $R'_1$ represents

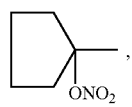

and each of $R'_2$ and $R'_3$ represents methyl, or $R'_2$ and $R'_3$ together represent —$(CH_2)_4$— or —$(CH_2)_5$—, $R'_4$ represents $(CH_3)_2CH$—;

or when $R'_1$ represents

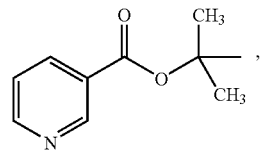

and each of $R'_2$ and $R'_3$ represents methyl, $R'_4$ represents $(CH_3)_2CH$— or $(CH_3)_2CH(CH_3)$—;

or when $R'_1$ represents

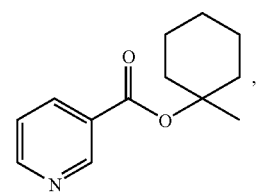

and each of $R'_2$ and $R'_3$ represents —$(CH_2)_5$—, $R'_4$ represents $(CH_3)_2CCH(CH_3)$—; or (5) when $R'_1$ represents cyclohexyl, and each of $R'_2$ and $R'_3$ represents methyl, $R'_4$ may represent

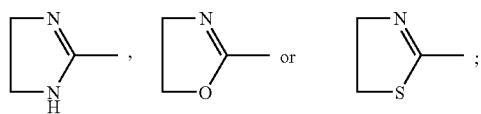

or when $R'_1$ represents cylclopentyl, and each of $R'_2$ and $R'_3$ represents —$(CH_2)_2$—, $R'_4$ may represent

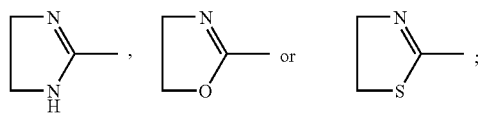

or when $R'_1$ represents isopropyl, and each of $R'_2$ and $R'_3$ represents methyl, $R'_4$ may represent

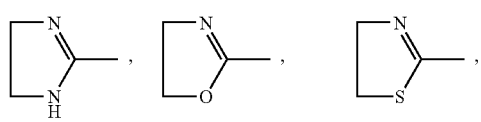

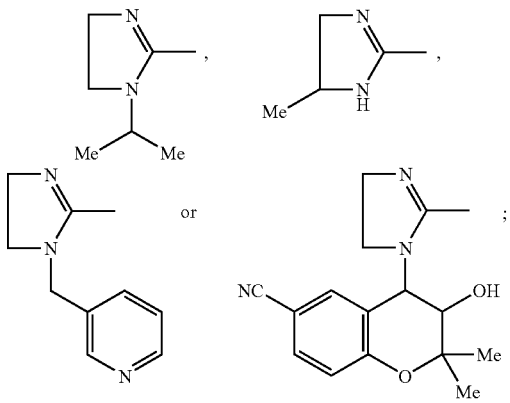

or (6) when R'$_1$ represents isopropyl, and each of R'$_2$ and R'$_3$ represents methyl, R'$_4$ may represent Val-, Trp-, Ile-, Leu-, Phe-, O$_2$N-Arg-, Pro-, Leu-Val-, Trp-Trp-Trp- or (CH$_3$)$_2$CH—SO$_2$—; or R$_4$' may represent tosyl, nicotinyl, 4-chlorobenzoyl, morphorinoacetyl, 3-thienylacetyl, or 3-indolylacetyl; or when R'$_1$ represents cyclopropyl, and each of R'$_2$ and R'$_3$ represents —(CH$_2$)$_2$—, R'$_4$ represents Val-; or when R'$_1$ represents cyclohexyl, and each of R'$_2$ and R'$_3$ represents methyl, R'$_4$ represents Pro-; or when R'$_1$ represents cyclohexyl, and each of R'$_2$ and R'$_3$ represents —(CH$_2$)$_2$—, R'$_4$ represents Pro- or nicotinyl.

According to the invention, the amine derivatives represented by formula I$_a$, its isomers, racemes or optical isomers, and its acid addition salts are also useful in the prophylaxis or treatment of cardiovascular diseases, diabetes, bronchial and urinary smooth muscle spasm, wherein examples of the acid addition salts are the salts with inorganic acids such as hydrochloric acid, sulfuric acid, phosphoric acid, hydrobromic acid; and the salts with organic acids such as acetic acid, oxalic acid, citric acid, gluconic acid, succinic acid, tartaric acid, tosylic acid, methanesulfonic acid, benzoic acid, lactic acid, maleic acid, nicotinic acid, cinnamic acid or 3-hydroxy-3-methylglutaric acid. The preferable salts of the amine derivative represented by formula I$_a$ are salts with hydrochloric acid, maleic acid, tosylic acid, cinnamic acid, and 3-hydroxy-3-methylglutaric acid.

Specifically, for the amine derivative represented by formula I in this invention, each of R$_1$, R$_2$ and R$_3$ may or may not be the same, and independently represents hydrogen, saturated or unsaturated, linear or branched aliphatic hydrocarbyl of 1 to 20 carbons, C$_{3-20}$ cycloalkyl, substituted C$_{3-20}$ cycloalkyl, C$_{5-20}$ aryl, substituted C$_{5-20}$ aryl, C$_{5-20}$ heterocyclohydrocarbyl, substituted C$_{5-20}$ heterocyclohydrocarbyl, α-hydroxy C$_{2-20}$ alkyl, α-C$_{1-10}$ alkylcarboxy C$_{1-10}$ alkyl, α-C$_{6-14}$ arylcarboxy C$_{1-10}$ alkyl, α-substitutedC$_{6-14}$ arylcarboxy C$_{1-10}$ alkyl, α-C$_{1-10}$ alkoxy C$_{1-10}$ alkyl, α-substituted C$_{5-10}$ aryloxy C$_{1-10}$ alkyl, α-amino C$_{1-20}$ alkyl, α-C$_{1-10}$ alkylamino C$_{1-10}$ alkyl, α-C$_{5-14}$ arylamino C$_{1-10}$ alkyl, α-substitutedC$_{5-14}$ arylamino C$_{1-10}$ alkyl, α-C$_{1-10}$ alkylamido C$_{1-10}$ alkyl, α-C$_{6-14}$ arylamido C$_{1-10}$ alkyl, α-substitutedC$_{6-14}$ arylamido C$_{1-10}$ alkyl;

R$_4$ represents hydrogen, methyl, ethyl, n-propyl, isopropyl, substituted cyclopropyl, substituted cyclobutyl, substituted cyclopentyl, substituted cyclohexyl, cyclopropylmethyl, cyclopentylmethyl, cyclohexylmethyl, α-(1-propenyl), 2-(1-butenyl), 3-(1-butenyl), cyclopentenyl, cyclohexenyl; or R$_4$ represents aryl and substituted aryl such as phenyl, substituted phenyl, o-nitrophenyl, m-nitrophenyl, p-nitrophenyl, 2,4-dinitrophenyl, 3,5-dinitrophenyl, 2,6-dinitropheenryl; heterocyclo and substituted heterocyclo, such as 3-pyridyl, 4-pyridyl, 3-furanyl, 3-thienyl, 3-pyrrolyl, oxazolinyl, thiazolinyl, pyrazolinyl, dihydrooxazolyl, dihydrothiazolinyl, dihydropyrazolinyl, N-substituted acylpyrazolinyl, N-substituted acyldihydrooxazoliyl, N-substituted dihydropyrrolinyl, imidazolyl, substituted imidazolyl; α-substituted arylalkyl, e.g. α-substituted arylmethyl, α-substituted arylethyl, α-substituted arylpropyl, α-substituted arylbutyl and α-substituted arylcycloalkyl; or R$_4$ represents natural or unnatural amino acid residues, substituted natural or unnatural amino acid residues, for example, Ala, Val, Leu, Ile, Phe, Asn, Glu, Trp, Tyr, Pro, Ser, Thr, Hyp, Cys, Met, Asp, Lys, Arg, His, O$_2$N-Arg; small peptide fragments consisting of natural or unnatural amino acid and substituted natural or unnatural amino acid, e.g. Cys-Cys, Arg-Arg-Arg, Pro-Arg-Asp, etc.; or R$_4$ represents aroyl, substituted aroyl; sulfinyl, e.g. alkylsulfinyl arylsulfinyl; sulfonyl e.g. alkylsulfonyl and arylsulfonyl; substituted vinyl, e.g. α-arylamino-β-nitroethenyl and α-aryl-β-cyanoethenyl; substituted carboimidyl, e.g. N-aryl-N'-nitro-carboimidyl and N-aryl-N'-nitromethyl-carboimidyl, or R$_4$ represents alkanoyl, e.g. propionyl, butanoyl and isobutanoyl etc.; heteroaroyl, e.g. 4-pyridylformyl, 3-pyrrolylacetyl, 3-indolylformyl, 3-indolylacetyl, 2-pyrrolylformyl and 3-pyrrolylacetyl, etc.; substituted heteroaroyl, e.g. 4-(2-nitro)-pyridylformyl, 3-(5-nitro)-pyridylformyl, 3-(5-hydroxy)-indolylformyl and 3-(5-methoxy)indolylacetyl, etc.; alkylamino-alkanoyl, e.g. dimethylaminoacetyl, dimethylaminopropionyl, diethylaminoacetyl, diethylaminopropionyl, di-(isopropyl)amino-propionyl, 2-tropylformyl, 2-tropenylformyl, 3-tropylformyl, 3-tropenylformyl, N-piperazinylformyl, N-benzoyl-1-piperazinylformyl, 1-tetrahydropyrrolyformyl, 1-tetrahydropyrrolylacetyl, 1-tetrahydropyrrolypropionyl, 1-hexahydropyridylformyl, 1-hexahydropyridylacetyl, 1-tetrahydropyridylpropionyl, 1-hexahydropyridylformyl, 1-hexahydropyridylacetyl, 1-hexahydropyridylpropionyl, di(cyclohexyl)-aminoacetyl, di(cyclohexyl)aminopropionyl, 1-(4-hydroxy)hexahydropyridylacetyl and 1-(4-hydroxy)hexahydropyridylpropionyl, etc.; alkylsulfinyl, e.g. methylsulfinyl, ethylsulfinyl, isopropylsulfinyl and N-morpholinylethyl sulfinyl, etc.; alkylsulfuryl, e.g. methylsulfuryl, ethylsulfuryl, isopropylsulfuryl and N-morpholinylethylsulfuryl, etc.; arylsulfuryl, e.g. phenylsulfuryl-3-pyridylsulfuryl, 4-pyridylethylsulfuryl and p-tolylsulfuryl, etc.; α-arylamino-β-nitroethenyl, e.g. α-(3-pyridyl)amino-β-nitroethenyl, α-(4-pyridyl) amino-β-nitroethenyl, α-(6-amino-3-pyridyl)amino-β-nitroethenyl, α-(3-nitrophenyl)amino-β-nitroethenyl, α-(3-carboxyphenyl)amino-β-nitroethenyl, α-(3-cyanophenyl)amino-β-nitroethenyl, α-(3-trifluoromethylphenyl)amino-β-nitroethenyl, and α-(3,4-dihalophenyl) amino-β-nitroethenyl, etc.; α-arylamino-β-cyanoethenyl, e.g. α-(3-pyridyl)amino-β-cyanoethenyl, α-(4-pyridyl)amino-β-cyanoethenyl, α-(6-amino-3-pyridyl)amino-β-cyanoethenyl, α-(3-nitrophenyl)amino-β-cyanoethenyl, α-(3-carboxyphenyl)amino-cyanoethenyl, α-(3-cyanophenyl) amino-β-cyanoethenyl, α-(3-trifluoromethylphenyl)amino-β-cyanoethenyl, and α-(3,4-dihalophenyl)amino-β-cyanoethenyl, etc.; N-aryl-N'-nitro-carboimidyl, e.g. N-(3-pyridyl)-N'-nitro-N'-carboimidyl, N-(3-nitrophenyl) —N'-nitro-N'-carboimidyl and N-(3-halophenyl)-N'-nitro-N'-carboimidyl, etc.; N-aryl-N'-nitromethyl-carboimidyl, e.g. N-(3-pyridyl)-N'-nitromethyl-N'-carboimidyl, α-aryl-β-nitroethenyl, e.g. α-(3-pyridyl)-β-nitroethenyl, α-(4-pyridyl)-β-nitroethenyl, α-(6-amino-3-pyridyl)-β-nitroethenyl, α-(4-nitropyridyl)-β-nitroethenyl, α-(3-cyanophenyl)-β-nitroethenyl, α-(3,4-dihalophenyl)-β-nitroethenyl, ect.; α-aryl-β-cyanoethenyl, e.g. α-(3-pyridyl)-β-cyanoethenyl, α-(4-pyridyl)-β-cyanoethenyl, α-(6-amino-3-pyridyl)-β-cyanoethenyl, α-(3-nitropyridyl)-β-cyanoethenyl, α-(3-cyanophenyl)-β-cyanoethenyl, α-(3-trifluoromethylphenyl)-β-cyanoethenyl and α-(3,4-dihalophenyl)-β-cyanoethenyl; or $R_4$ represents α-heterocyclo-β-nitroethenyl and α-heterocyclo-β-cyano-ethenyl, wherein the heterocyclo substituent may be 4-benzopyranyl, 4-pyridopyranyl or 4-thienopyranyl in which position 2 is substituted with 2,2-dimethyl, spiropentyl or spirohexyl; positions 3 and 4 are dehydrogenated or 3-hydroxy; position 6 is substituted with an electron withdrawing group such as nitro, cyano, trifluoromethyl, pentofluoroethyl, sulfamoyl and methylsulfonyl, etc.

When $R_1$ represents alkyl, cycloalkyl, α-aminoalkyl, α-aminocycloalkyl or aryl, $R_2$ and $R_3$ each represents alkyl or alkylene, and $R_4$ represents alkyl, alkylaminoalkyl, alkenyl, cycloalkyl, alkyoxycarbonyl or arylalkyl, the preferred compound represented by formula I is shown in Table 1.

TABLE 1 the preferred compound represented by formula I wherein each of the substituents is hydrocarbyl

| compound | $R_1$ | $R_2$ | $R_3$ | $R_4$ | formula |
|---|---|---|---|---|---|
| 1 | $(CH_3)_2CH-$ | $CH_3-$ | $CH_3-$ | $(CH_3)_2CH-$ | $C_9H_{21}N$ |
| 2 | $(CH_3)_2CH-$ | $CH_3-$ | $CH_3-$ | $H-$ | $C_6H_{15}N$ |
| 3 | $(CH_3)_2CH-$ | $CH_3-$ | $CH_3-$ | $CH_3-$ | $C_7H_{17}N$ |
| 4 | $(CH_3)_2CH-$ | $CH_3-$ | $CH_3-$ | $C_2H_5-$ | $C_8H_{19}N$ |
| 5 | $(CH_3)_2CH-$ | $CH_3-$ | $CH_3-$ | $CH_3CH_2CH_2-$ | $C_9H_{21}N$ |
| 6 | $(CH_3)_2CH-$ | $CH_3-$ | $CH_3-$ | $n-C_4H_9-$ | $C_{10}H_{23}N$ |
| 7 | $(CH_3)_2CH-$ | $CH_3-$ | $H-$ | $(CH_3)_2CH-$ | $C_8H_{19}N$ |
| 8 | $H-$ | $H-$ | $H-$ | $(CH_3)_2CH-$ | $C_4H_{11}N$ |
| 9 | $C_2H_5-$ | $CH_3-$ | $CH_3-$ | $(CH_3)_2CH-$ | $C_6H_{15}N$ |
| 10 | $C_2H_5-$ | $CH_3-$ | $H-$ | $H-$ | $C_4H_{11}N$ |
| 11 | $C_2H_5-$ | $CH_3-$ | $CH_3-$ | $CH_3-$ | $C_6H_{15}N$ |
| 12 | $C_2H_5-$ | $CH_3-$ | $H-$ | $H-$ | $C_4H_{11}N$ |
| 13 | $(CH_3)_2CH-$ | $CH_3-$ | $CH_3-$ | $(CH_3)_2CHCH_2-$ | $C_{10}H_{23}N$ |
| 14 | $(CH_3)_2CH-$ | $CH_3-$ | $CH_3-$ | $t-C_4H_9-$ | $C_{10}H_{23}N$ |
| 15 | $(CH_3)_2CH-$ | $CH_3-$ | $CH_3-$ |  | $C_{10}H_{21}N$ |
| 16 | $(CH_3)_2CH-$ | $CH_3-$ | $CH_3-$ | $(CH_3)_2NCH_2CH_2-$ | $C_{10}H_{24}N_2$ |
| 17 | $Ph-$ | $CH_3-$ | $CH_3-$ | $CH_3OCOCH_2-$ | $C_{12}H_{17}NO_2$ |
| 18 | $Ph-$ | $CH_3-$ | $C_2H_5-$ | $(CH_3)_2NCH_2CH_2-$ | $C_{14}H_{24}N_2$ |
| 19 | $Ph-$ | $CH_3-$ | $(CH_3)_2CH-$ | $(CH_3)_2CH-$ | $C_{14}H_{23}N$ |
| 20 | $Ph-$ | $CH_3-$ | $CH_3-$ | $CH_3CH_2CH_2-$ | $C_{12}H_{19}N$ |
| 21 | $Ph-$ | $C_2H_5-$ | $CH_3-$ | $CH_3CH_2CH_2-$ | $C_{13}H_{21}N$ |
| 22 | $Ph-$ | $(CH_3)_2CH-$ | $CH_3-$ | $CH_3CH_2CH_2-$ | $C_{14}H_{23}N$ |
| 23 | $(CH_3)_2CH-$ | $CH_3-$ | $CH_3-$ | $CH_3OCOCH_2-$ | $C_9H_{19}NO_2$ |
| 24 | $(CH_3)_2CH-$ | $CH_3-$ | $CH_3-$ | $PhCH_2-$ | $C_{13}H_{21}N$ |
| 25 | $(CH_3)_2CH-$ | $CH_3-$ | $CH_3-$ | $CH_2=CH-CH_2-$ | $C_9H_{19}N$ |
| 26 | $(CH_3)_2CH-$ | $CH_3-$ | $CH_3-$ | $(CH_3)_2CH-CH_2-$ | $C_{10}H_{23}N$ |
| 27 | $(CH_3)_2CH-$ | $CH_3-$ | $CH_3-$ | $((CH_3)_2CH)_2NCH_2CH_2-$ | $C_{14}H_{32}N_2$ |
| 28 | 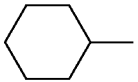 | $CH_3-$ | $CH_3-$ | $(CH_3)_2CH-$ | $C_{12}H_{25}N$ |
| 29 | 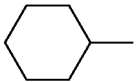 | $CH_3-$ | $CH_3-$ | $(CH_3)_2NCH_2CH_2-$ | $C_{13}H_{28}N_2$ |
| 30 | 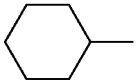 | $CH_3-$ | $CH_3-$ | $PhCH_2-$ | $C_{16}H_{25}N$ |
| 31 | 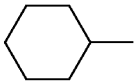 | $CH_3-$ | $CH_3-$ | $CH_3OCOCH_2-$ | $C_{12}H_{23}NO_2$ |
| 32 |  | $-CH_2-CH_2-$ | | $(CH_3)_2CH-$ | $C_9H_{17}N$ |
| 33 |  | $-CH_2-CH_2-$ | | $(CH_3)_2NCH_2CH_2-$ | $C_{10}H_{20}N_2$ |

TABLE 1-continued the preferred compound represented by formula I wherein each of the substituents is hydrocarbyl

| compound | $R_1$ | $R_2$ | $R_3$ | $R_4$ | formula |
|---|---|---|---|---|---|
| 34 |  | —$CH_2$—$CH_2$— | | $PhCH_2$— | $C_{13}H_{17}N$ |
| 35 |  | —$CH_2$—$CH_2$— | | $CH_3OCOCH_2$— | $C_9H_{15}NO_2$ |
| 36 | $(CH_3)_2C$—<br>    \|<br>   $NH_2$ | $CH_3$— | $CH_3$— | $(CH_3)_2CH$— | $C_9H_{22}N_2$ |

When $R_1$ represents alkyl, cycloalkyl, α-amidoalkyl or α-amidocycloalkyl, $R_2$ and $R_3$ each represents alkyl or alkylene, and $R_4$ represents amino acid residue, small peptide, sulfonyl, aroyl and heterocycloacyl, the preferred compound represented by formula I is shown in Table 2.

TABLE 2 the preferred compound represented by formula I wherein an acyl substituent presents in the formula

| compound | $R_1$ | $R_2$ | $R_3$ | $R_4$ | formula |
|---|---|---|---|---|---|
| 37 | $(CH_3)_2CH$— | $CH_3$— | $CH_3$— | Val- | $C_{11}H_{24}N_2O$ |
| 38 | $(CH_3)_2CH$— | $CH_3$— | $CH_3$— | 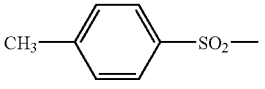 | $C_{13}H_{21}N_2OS$ |
| 39 | $(CH_3)_2CH$— | $CH_3$— | $CH_3$— | 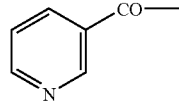 | $C_{12}H_{28}N_2O$ |
| 40 | $(CH_3)_2CH$— | $CH_3$— | $CH_3$— | Trp- | $C_{17}H_{25}N_3O$ |
| 41 | $(CH_3)_2CH$— | $CH_3$— | $CH_3$— | Ile- | $C_{12}H_{26}N_2O$ |
| 42 | $(CH_3)_2CH$— | $CH_3$— | $CH_3$— | Leu- | $C_{12}H_{26}N_2O$ |
| 43 | $(CH_3)_2CH$— | $CH_3$— | $CH_3$— | Phe- | $C_{15}H_{24}N_2O$ |
| 44 | $(CH_3)_2CH$— | $CH_3$— | $CH_3$— | $O_2N$-Arg- | $C_{12}H_{26}N_6O_3$ |
| 45 | $(CH_3)_2CH$— | $CH_3$— | $CH_3$— | Pro- | $C_{11}H_{22}N_2O$ |
| 46 | $(CH_3)_2CH$— | $CH_3$— | $CH_3$— | Leu-Val- | $C_{17}H_{35}N_3O_2$ |
| 47 |  | —$CH_2$—$CH_2$— | | Val- | $C_{11}H_{20}N_2O$ |
| 48 | $(CH_3)_2CH$— | $CH_3$— | $CH_3$— | Trp-Trp-Trp- | $C_{39}H_{45}N_7O_3$ |
| 49 | 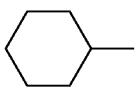 | $CH_3$— | $CH_3$— | Pro- | $C_{14}H_{26}N_2O$ |
| 50 | 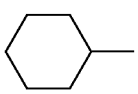 | —$CH_2$—$CH_2$— | | Pro- | $C_{14}H_{24}N_2O$ |
| 51 | $(CH_3)_2CH$— | $CH_3$— | $CH_3$— | $(CH_3)_2CHSO_2$— | $C_9H_{21}N_2OS$ |
| 52 | $(CH_3)_2CH$— | $CH_3$— | $CH_3$— | 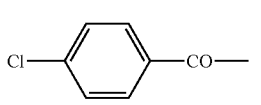 | $C_{13}H_{18}ClNO$ |

TABLE 2-continued the preferred compound represented by formula I wherein an acyl substituent presents in the formula

| compound | R₁ | R₂ | R₃ | R₄ | formula |
|---|---|---|---|---|---|
| 53 | $(CH_3)_2CH$— | $CH_3$— | $CH_3$— |  | $C_{12}H_{24}N_2O_2$ |
| 54 | $(CH_3)_2CH$— | $CH_3$— | $CH_3$— | 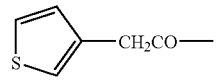 | $C_{12}H_{19}NOS$ |
| 55 | $(CH_3)_2CH$— | $CH_3$— | $CH_3$— | 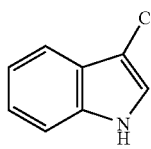 | $C_{16}H_{22}N_2O$ |
| 56 | 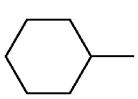 | —$CH_2$—$CH_2$— | | 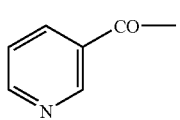 | $C_{15}H_{20}N_2O$ |
| 57 | 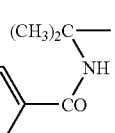 | $CH_3$— | $CH_3$— | $(CH_3)_2CH$— | $C_{16}H_{26}ClN_2O$ |

When $R_2$, $R_3$ and $R_4$ each represents alkyl or alkylene, and $R_1$ represents α-hydroxyalkyl, α-hydroxycycloalkyl or nitrate thereof, the preferred compound of formula I substituted with an alcohol or ester thereof is shown in Table 3.

TABLE 3 the preferred compound represented by formula I wherein the substituents comprise an alcohol or ester thereof

| compound | R₁ | R₂ | R₃ | R₄ | formula |
|---|---|---|---|---|---|
| 58 |  | $CH_3$— | $CH_3$— | $(CH_3)_2CH$— | $C_9H_{21}NO$ |
| 59 |  | $CH_3$— | $CH_3$— | $(CH_3)_3CCH$—<br>\|<br>$CH_3$ | $C_{12}H_{27}NO$ |
| 60 | 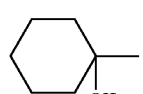 | $CH_3$— | $CH_3$— | $(CH_3)_2CH$— | $C_{12}H_{25}NO$ |
| 61 | 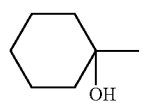 | —$(CH_2)_5$— | | $(CH_3)_2CH$— | $C_{15}H_{29}NO$ |
| 62 |  | $CH_3$— | $CH_3$— | $(CH_3)_2CH$— | $C_{11}H_{23}NO$ |
| 63 | 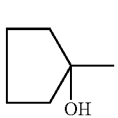 | —$(CH_2)_4$— | | $(CH_3)_2CH$— | $C_{13}H_{25}NO$ |

TABLE 3-continued the preferred compound represented by formula I wherein the substituents comprise an alcohol or ester thereof

| compound | $R_1$ | $R_2$ | $R_3$ | $R_4$ | formula |
|---|---|---|---|---|---|
| 64 | $(CH_3)_2C(ONO_2)-$ | $CH_3-$ | $CH_3-$ | $(CH_3)_2CH-$ | $C_9H_{20}N_2O_3$ |
| 65 | 1-nitrooxy-1-methylcyclohexyl | $CH_3-$ | $CH_3-$ | $(CH_3)_2CH-$ | $C_{12}H_{24}N_2O_3$ |
| 66 | 1-nitrooxy-1-methylcyclopentyl | $CH_3-$ | $CH_3-$ | $(CH_3)_2CH-$ | $C_{11}H_{22}N_2O_3$ |
| 67 | 1-nitrooxy-1-methylcyclohexyl | $-(CH_2)_5-$ | | $(CH_3)_2CH-$ | $C_{15}H_{28}N_2O_3$ |
| 68 | 1-nitrooxy-1-methylcyclopentyl | $-(CH_2)_4-$ | | $(CH_3)_2CH-$ | $C_{13}H_{24}N_2O_3$ |
| 69 | $(CH_3)_2C-$O-CO-(3-pyridyl) | $CH_3-$ | $CH_3-$ | $(CH_3)_2CH-$ | $C_{15}H_{24}N_2O_2$ |
| 70 | $(CH_3)_2C-$O-CO-(3-pyridyl) | $CH_3-$ | $CH_3-$ | $(CH_3)_3CCH(CH_3)-$ | $C_{18}H_{30}N_2O_2$ |
| 71 | 1-methyl-1-(nicotinoyloxy)cyclohexyl | $-(CH_2)_5-$ | | $(CH_3)_3CCH(CH_3)-$ | $C_{24}H_{38}N_2O_2$ |

When $R_1$, $R_2$ and $R_3$ each represents alkyl or cycloalkyl, and $R_4$ represents imidazolinyl, thiazolinyl or substituted imidazolinyl, the compound of formula I of which $R_4$ is heterocyclo is shown in Table 4

TABLE 4

The compound of formula I, wherein $R_4$ is heterocyclo.

| compound | $R_1$ | $R_2$ | $R_3$ | $R_4$ | formula |
|---|---|---|---|---|---|
| 72 | $(CH_3)_2CH-$ | $CH_3-$ | $CH_3-$ | 4,5-dihydro-2-imidazolyl (NH) | $C_9H_{19}N_3$ |
| 73 | $(CH_3)_2CH-$ | $CH_3-$ | $CH_3-$ | 4,5-dihydro-2-oxazolyl (O) | $C_9H_{18}N_2O$ |

TABLE 4-continued
The compound of formula I, wherein $R_4$ is heterocyclo.
| compound | $R_1$ | $R_2$ | $R_3$ | $R_4$ | formula |
|---|---|---|---|---|---|
| 74 | $(CH_3)_2CH-$ | $CH_3-$ | $CH_3-$ | 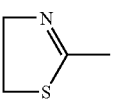 | $C_9H_{18}N_2S$ |
| 75 | 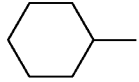 | $CH_3-$ | $CH_3-$ | 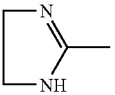 | $C_{12}H_{23}N_3$ |
| 76 | 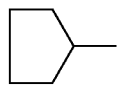 | $CH_3-$ | $CH_3-$ | 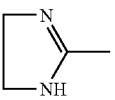 | $C_{11}H_{21}N_3$ |
| 77 | 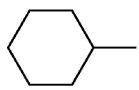 | $CH_3-$ | $CH_3-$ | 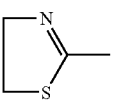 | $C_{12}H_{22}N_2S$ |
| 78 | 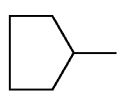 | $CH_3-$ | $CH_3-$ | 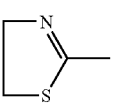 | $C_{11}H_{20}N_2S$ |
| 79 | 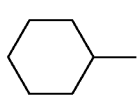 | $CH_3-$ | $CH_3-$ | 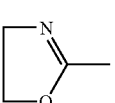 | $C_{12}H_{22}N_2O$ |
| 80 | 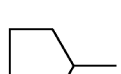 | $CH_3-$ | $CH_3-$ | 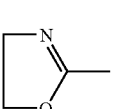 | $C_{11}H_{20}N_2O$ |
| 81 | $(CH_3)_2CH-$ | $CH_3-$ | $CH_3-$ | 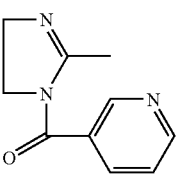 | $C_{15}H_{22}N_4O$ |
| 82 | $(CH_3)_2CH-$ | $CH_3-$ | $CH_3-$ | 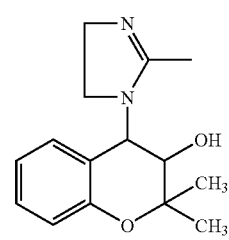 | $C_{21}H_{30}N_4O_2$ |
| 83 | $(CH_3)_2CH-$ | $CH_3-$ | $CH_3-$ | 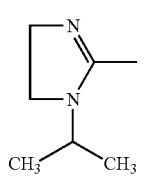 | $C_{12}H_{25}N_3$ |

TABLE 4-continued

The compound of formula I, wherein $R_4$ is heterocyclo.

| compound | $R_1$ | $R_2$ | $R_3$ | $R_4$ | formula |
|---|---|---|---|---|---|
| 84 | $(CH_3)_2CH-$ | $CH_3-$ | $CH_3-$ | 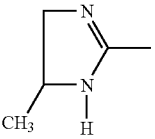 | $C_{10}H_{21}N_3$ |

Furthermore, $R_4$ may form cyclic compound with $R_1$, $R_2$ and $R_3$, such as cyclic analogues of the compounds shown in Table 1, 2 and 3. The preferred are 2,2,3,5-tetramethyltetrahydropyrrole, 2,2,3,6-tetramethylpiperidine, and 2,2,3,7-tetramethylaxacycloheptane, Moreover, the compound represented by formula $I_a$ can form an amide or an ester derivative with an organic acid, wherein said organic acid is preferably nicotinic acid, cinnamic acid, maleic acid, 2,4,5-trichlorophenoxyacetic acid and 3-hydroxy-3-methylglutaric acid.

According to this invention, one general procedure for preparing the compound represented by formula $I_a$ is as follows: a suitable primary amine $R'_1R'_2R'_3CNH_2$ and $R'_4X$ are heated and/or pressurized in a reactor in absence of solvent or in the presence of an organic solvent, wherein the organic solvent may be carbohydron, aromatic solvent or alcohol such as cyclohexane, pentane, hexane, heptane, octane, nonane, decane, duodecane, benzene, toluene, xylene, nitrobenzene, glycol, propanediol, propanetriol, etc.; In the case of an organic solvent used, a catalyst may or may not present the catalyst may be organic or inorganic base or alcohol such as potassium hydroxide, sodium hydroxide, pyridine, glycol, propanediol, propanetriol, low molecular weight polyglycol, etc.; the reaction temperature range is 50 to 400 degree of centigrade, preferably 110 to 250 degree of centigrade; The reaction pressure depends on the solvent used and the temperature, usually ranging from 0.1 to 20 million pascal, preferably from 0.5 to 15 million pascal. The reaction temperature can also be obtained by filling of nitrogen, helium, and argon, etc. The product is isolated and purified by general recrystalization and/or chromatography. Suitable pharmacentical salts may be produced by reacting the compound represented by formula Ia with an inorganic acid or organic acid, if deired.

According to the invention, the second procedure for preparing the compound represented by formula Ia is as follows: a primary amine $R'_1R'_2R'_3CNH_2$, an aldehyde or ketone of $R'_4$ and a catalyst are heated to 30-300° C. and/or pressurized to 0.1-20 MPa for hydrogenation in absence of or in the presence of an organic solvent, wherein $R_1'$, $R_2'$, $R_3'$ and $R_4'$ are defined as above, the catalyst may be palladium carbon, Raney nickel, platium oxide and nickel-copper, and said organic solvent may be excess amount of aldehyde or keltone of $R'_4$, toluene, xylene, 1,2-dichloroethane, 1,4-dioxane, dimethoxyethane, methanol and ethanol.

In the aforesaid procedure, the primary amine is prepared through hydrolysis of hydrocarbylurea $R'_1R'_2R'_3CNHCONH_2$, which is produced by reacting urea with alkene or alcohol of $R_1' R_2' R_3'C$ or the mixture of both and concentrated sulfuric acid in the presence of an organic acid at 20-200° C., wherein the organic acid is acetic acid, trifluoroacetic acid or methanesulfonic acid.

In the aforesaid procedures, when the compound represented by formula I is a secondary alkylamine, a secondary amide or a secondary sulfonamide, it can be prepared by a known method in the art, see M. S. Dunn, B. M. Smart., Org. Synth., 1963, Coll. Vol. IV: 55; Houben-Weyl., XI/2: 482; J. B. Hendrickson, R. Bergeron, Tetrahedron Lett., 1973: 3839. It can also be produced by forming an imine or Schiff base followed by reduction or catalytic hydrogenation, see D. M. Balcom, C. R. Noller, Org. Synth., 1963, Coll. Vol. IV: 603; Cesare Ferri, "Reaktionen der organischen Synthese", Stuttgart, 1978, p. 85. There are special methods for preparing a secondary amine, for example, the substituted secondary amine can be produced by reacting a Schiff base or an imine with a Grignard agent, see Klusener P. A. A, Tipl and Brandsma, Tetrahedron, 1991, 2041; Klusener P. A. A, J. Chem. Soc., Chem. Commun., 1985, 1677.

When the secondary amine represented by formula I has a α-substituent of hydroxy or amino, it can be produced by reacting an epoxy compound or an aziridine derivative with a primary amine, see O. C. Dermer, G. E. Ham. "Ethylenimine and other Aziridines", Academic Press, New York, 1969; L. B. Clapp, J. Amer. Chem. Soc., 1948, 70: 184.

When $R_4$ of formula I represents an amino acid residue or a small peptide consisting thereof, the compound herein can be produced by a known method termed as protection-condensation-deprotection, see Ming Zhao, Chin. J. Med. Chem., 1995, 5(2): 91; Gu Mingdi, Peng Shipi, Yu Xuemin, J. Chin. Pharm. Sci., 1993, 2(2): 102.

When $R_4$ of formula I represents hydrogen, the compound (i.e. a primary amine) can be prepared by hydrolysis of a corresponding amide produced through a Ritter reaction, see U.S. Pat. No. 1972, 3673249. This invention further provides, a method for preparation of a primary amine, which comprises reacting urea with a corresponding alkene or alcohol or a mixture of both and concentrated sulfuric acid in the presence of an organic acid at a temperature ranging from 20 to 200 degree of centigrade, wherein the organic acid may be acetic acid, trifluoroacetic acid or methanesulfonic acid, followed by hydrolysis of the hydrocarbylurea with a catalyst, such as an acid, a base etc.

According to the invention, the compound represented by formula I or $I_a$ can exist in the form of stereoisomers. The chiral center of the compound represented by formula I may be in configuration of S- or R-. The invention includes all possible stereoisomers such as enantiomers or diastereomers, and the mixture of two or more stereoisomers such as the mixture of enantiomers and/or diastereomers in any desired proportion. Therefore, the invention relates to enantiomers such as pure levo-enantiomer or dextro-enantiomer, and the mixture of both forms in any proportion or racemes. If there are cis-/trans-isomers, the invention also relates to the cis-form and trans-form and the mixture of both forms. If needed, the desired pure stereoisomer can be prepared by general resolution of the mixture or: by, stereospecific synthesis. If there is a movable hydrogen, the invention also relates to tautomers.

According to the invention, the compound represented by formula I and its stereoisomers show excellent effects in prophylaxis or treatment of cardiovascular diseases such as hypertension, arrhythm, angina diaphragmatic, congestive heart failure, and myocardial infarction, diabetes, bronchial and urinary smooth muscle spasm. Therefore, they can be used as drugs for prophylaxis or treatment of cardiovascular diseases of animals, preferably of mammalian, especially of man.

Therefore, the invention also relates to pharmaceutical compositions containing as an active component an effective amount of at least one compoumd represented by formula I or $I_a$, or its pharmaceutical salts and/or its stereoisomers, and conventional excipients or adjuvants. Usually, the pharmaceutical composition, of this invention contains 0.1 to 90 percent weight of the compound of formula I or Ia, or its physiologically acceptable salts. The pharmaceutical composition can be prepared according to the known method of this field. For use as medicaments, the compound of formula I or $I_a$ and/or its stereoisomer may be fomulated into proper forms or dosages for administration to man by combination with one or more solid or liquid excipient and/or adjuvant, if needed.

The compound of formula I or $I_a$ in this invention, or its pharmaceutical composition can be administered in a single dosage form through enteral or parenteral routes, such as oral, intramuscular, subcutaneous, nasal, oral mucosal, cutaneous, peritoneal or rectal administration. Such medicaments can be formualted into tablets, capsules, drops, aerosols, pills, powders, solutions, suspensions, emulsions, granules, liposomes, patches, buccal tablets, suppositories, lyophilized powders for injection, and so on. It can be formulated into ordinary preparation, delayed release preparation, controlled release preparation, and various microparticle delivery system. In order to formulate a single dose of medicaments into tablets, the well-known carriers can be extensively used. Examples of carriers are as follows: diluents and absorbents such as starch, dextrine, calcium sulfate, lactose, mannitol, sucrose, sodium chloride, glucose, urea, calcium carbonate, kaolin, avicel, aluminium silicate, etc.; humectans and adherents such as water, glycerol, polyethylene glycol, ethanol, propanol, starch paste, dextrine, syrup, honey, glucose solution, acacia paste, gelatin paste, sodium carboxymethyl cellulose, lac, methyl cellulose, potassiun phosphate, polyvinyl pyrrolidone, etc.; disintegrating agent such as droughty starch, alginate, agar powder, laminaran, sodium hydrocarbonate, citric acid, calcium carbonate, polyoxyethylenesorbol fatty acidic ester, sodium dodecyl sulphate, methyl cellulose, ethyl cellulose, etc.; disintegratation inhibitors such as sucrose, glycerol tristearate, cocoa oil, hydrgenated oil, etc.; absorbent accerelants such as quarternary ammonium salts, sodium lauryl sulfate, etc.; lubricants such as talc, silica, cornstarch, stearate, boric acid, liquid wax, polyglycol, etc. The tablets can be further formulated into coating tablets such as sugar coating, film coating, enteral dissolution coating, or double-layered tablets and multi-layered tablets. In order to formulate a single dose of medicaments into pills, the well-known carriers can be extensively used. Examples of such carriers are as follows: diluents and absorbents such as glucose, lactose, starch, cocoa fat, hydrogenated vegetable oil, polyvinyl pyrrolidone, gelucire, kaolin, talc etc.; adherents such as acacia, bassora gum, gelatin, ethanol, honey, liquid sugar, rice paste or flour paste, etc.; disintegrating agents such as agar powder, droughty starch, alginate, sodium dodecyl sulphate, methyl cellulose, ethyl cellulose, etc. In order to formulate a single dose of medicaments into suppositories, the well-known carriers can be extensively used. Examples of such carriers are as follows: polyglycol, lecithin, cocoa fat, higher alcohol, ester of higher alcohol, gelatin, semi-synthesized glyceride, etc. In order to formulate a single dose of medicaments into capsules, the active compound of formula I or $I_a$ or its stereoisomers can be admixtured with the aforesaid carriers, and the resulting mixture cans be capsuled into hard gelatin capsules or soft capsules. The active compound of formula I or Ia or its stereoisomers can also be formulated into microcapsules.

Microcapsules can be suspended in aqueous solution and formulated into suspensions, or encapsuled in hard capsules, or formulated into injectable preparations. In order to produce injectable preparations such as solutions, emulsions, lyophilized powder for injection and suspensions, all the diluents commonly used in the art can be used, for examples, water, ethanol, polyglycol, 1,3-propanediol, ethoxylated isostearol, polyoxidized isostearol, polyoxyethylene sorbol fatty acidic ester, etc. In addition, in order to prepare isosmotic solutions, the injectable preparations can be appended proper amount of sodium chloride, glucose or glycerol; furthermore, they can also be added with conventional cosolvent, buffers, pH modulator, etc.

Moreover, the medicaments can also be appended colorants, antiseptics, flavors, condiments, sweets, or others, if needed.

The administration dosage of the compound of fomula I or Ia in this invention, its pharmaceutical salts or its stereoisomers depends on many factors, including the property and severity of the diseases to be prevented or to be treated, sex, age, body weight and individual responsiveness of the animal or patient, the specific compound used, administration routes, and administration times, etc. The aforesaid dosage can be a single dosage form or multiple dosage forms such as two, three or four dosage forms.

EXAMPLES

The following examples illustrate the present invention more specifically, but that does not mean any limitation to the invention.

Example 1

Production of N-(1-methylethyl)-2,3-dimethyl-2-butylamine (Compound 1): Method 1. The solution of 7.6 g (0.0745 mole) 2,3-dimethyl-2-butanol in 3.24 mL glacial acetic acid was cooled and maintained at −5 to −8 degree of centigrade (° C.), then was added 7.3 g (0.49 mole) of powdered potassium cyanide in several times under stirring. 32.4 mL concentrated sulfuric acid was added dropwise while keeping the temperatue below 20 ° C., after which, the reaction mixture was stirred for 3.5 hours below 20° C. and another 6 hours at room temperature, then stood overnight. After poured into ice colded water, the mixture was adjusted to pH10 with 20% aqueous sodium hydroxide solution, and extracted with ether (×4). The extract was dried over anhydrous sodium sulfate. After filtration on the next day, the dessicator was removed, and the filtrate was evaporated off the ether, then distilled in vacuum to give 8.8 g (yield 91.6%) N-[2-(2,3-dimethylbutyl)]-fomide; bp 105-108° C./5 mmHg.

To the mixture of 7.7 g (0.0597 mole) N-[2-(2,3-dimethylbutyl)]-formide, 6.2 mL ethanol and 51.6 mL wate, 17.4 mL concentrated hydrochloric acid was added. The reaction mixture was refluxed for 4 hours in the oil bath, then distilled off ethanol in vacuum. The residue was adjusted to above pH12 with 40% aqueous sodium hydroxide solution, and extracted with ether. The extract was dried over anhydrous potassiun carbonate. After recovering the ether, The residue was distilled at atmosphere to give 3.75 g (yield 62.2%) 2,3-dimethyl-2-butylamine, bp 97-104° C.

The mixture of 10.6 g (0.15 mole) 2,3-dimethyl-2-butylamine, 6.45 g (0.0524 mole) 2-bromopropane, 3.0 mL glycol and 22.0 mL toluene was added into an autoclave, and heated with stirring for 17 hours at temperature of 170° C., after which, the organic layer was separated and extracted with 6N hydrochloric acid (15 mL×4). The extract was combined and washed once with toluene, then adjusted to pH 12-13 with 4% aqueous sodium hydroxide in the ice bath. The mixture was extracted with ether and then dried over anhydrous potassium carbonate. After recovering the ether, The filtrate was distilled to yield the fraction of bp 135-145° C. (yield 68.8%). The hydrochloride's Mp is 228-230° C. (i-PrOH-Et$_2$O). Elemental analysis for C$_9$H$_{22}$ClN(%): Calculated C, 60.14; H, 12.34; N, 7.79, Cl 19.73. Found C, 60.14; H, 12.48; N, 7.31, Cl 19.67. $^1$H-NMR(D$_2$O, ppm) 0.98(d, J=6.75H, 6H), 1.33(s, 6H), 1.37(d, J=6.46, 6H), 2.10(m, 1H), 3.70(m, 1H). MS(m/z) 143 (M+), 100(B).

Method 2. To the mixture of 288 mL glacial acetic acid, 412 g (6.86 mole) urea and 288 g (3.43 mole) 2,3-dimethyl-2-butene, the solution of 412 mL concentrated sulfuric acid and 412 mL of glacial acetic acid was added dropwise under stirring, while maintaining the reaction temperature at the range of 45° C. to 50° C., then stirred for 5 hours at the temperature of 50-55° C. The mixture stood overnight. Next day, the mixture was reacted for another 7 hours at the temperature of 50-55° C., then poured into the solution of 1200 g (30 mole) sodium hydroxide in 8 L glacial water. The resulting solid was filtered, washed with water (200 mL×5) and dried to give 404 g (yield 81.8%) N-(2,3-dimethyl-2-butyl)urea as white solid, mp 175-176° C. Elemental analysis for C$_7$H$_{16}$N$_2$O(%): Calculated C, 58.30; H, 11.18; N, 19.42. Found C, 58.70; H, 11.54; N, 19.25. $^1$H-NMR(CDCl$_3$, ppm) 0.88-0.91(d, 6H, 2×CH$_3$), 1.26(s, 6H, 2×CH$_3$), 2.20-2.26(m, 1H, CH), 4,45(br, 2H), 4.65(br, 1H). MS(m/z) 145.0, 144.0 (M$^+$), 143.0, 129.1, 101.0, 86.1, 69.1, 58.0(B).

To the mixture of 196 g (1.36 mole) N-(2,3-dimethyl-2-butyl)urea and 392 mL glycol or tri-(ethanol)amine, a solution of 118 g (2.95 mole) sodium hydroxide in 118 mL water was added. The reaction mixture was heated for 8 hours in an oil bath at temperature of 120° C., then distilled at atmosphere to collect the fraction of bp 95-102° C. To the fraction, 75 g anhydrous potassium carbonate and. 40 g sodium hydroxide were added. The resulting mixture was distilled to give 88.5 g (yield 64.3%) 2,3-dimethyl-2-butylamine as colorless liquid, bp 99-101° C. $^1$H-NMR(CDCl$_3$, ppm) 0.88-0.91(d, 6H, 2×CH$_3$), 1.04 (s, 6H, 2×CH$_3$), 1.53(m, 1H, CH).

To a 50.0 ml autoclave, 10.6 g (0.15 mole) 2,3-dimethyl-2-butylamine, 6.45 g (0.0524 mol) 2-bromopropane, 3.0 ml glycol and 22.0 ml toluene were added, and heated with stirring for 17 hours at 170° C., after which the organic layer was seperated and extracted with 6N hydrochloric acid (15 ml×4). The extract was combined and washed once with toluene, then adjusted to pH 12-13 with 4% aqueous sodium hydroxide in the ice bath. The mixture was extracted with ether and then dried over anhydrous potassium carbonate the ether was recovered, and distilled to give the fraction of bp 135-145° C. (yield 68.8%). mp of the hydrochloride is 228-230° C., (i-PrOH: Et$_2$O). Elemental analysis for C$_9$H$_{22}$ClN (%): Calculated C, 60.14; H, 12.34; N, 7.79; Cl, 19.73. Found C, 60.14; H, 12.48; N, 7.31; Cl 19.67. $^1$H-NMR(D$_2$O, ppm) 0.98(d, J=6.75H, 6H), 1.33(s, 6H), 1.37(d, J=6.46, 6H), 2.10 (m, 1H), 3.70(m, 1H). MS(m/z) 143 (M$^+$), 100(B).

Method 3. a solution of 0.10 mole enamine (prepared from the condensation of methyl iso-propyl ketone and iso-propylamine) in 20 mL hexane was filled with N$_2$ and added dropwise to a solution containing 0.10 mole lithium methide with stirring in ice bath. After the reaction is complete, the mixture was poured into 500 g glacial water, and stirred. The aqueous layer was extracted with ether (×2). The resulting organic layer was concentrated. 3N hydrochloric acid was added to acified the organic layer to pH<1. The mixture was kept for ten minutes and adjusted to pH>11 with 10% aqueous sodium hydroxide, then extracted with ether (×3). The extract was dried over anhydrous potassium carbonate and filtered. The filtrate was distilled at atmosphere to give a fraction of bp 140-145° C. with a yield of 80%.

Example 2

Preparation of N-propyl-2,3-dimethyl-2-butylamine (compound 5)

To a solution of 8.25 g (0.15 mole) propionitrile in 25 mL glacial acetic acid, 15 g concentrated sulfuric acid was added dropwise while controlling the reaction temperature at about 38° C., then 5.2 g (0.051 mole) of 2,3-dimethyl-2-butanol was added dropwise at the temperature below 40° C. with stirring. The mixture was stirred overnight while maintaining the temperature, then poured into glacial water, basified with 40% sodium hydroxide solution and extracted with ether. The ether extract was combined, washed once with water, and dried over anhydrous magnesium sulfate. After recovering the ether, 6.2 g light yellow liquid was obtained and solved in 80 mL anhydrous ether. The resulting solution was added dropwise to a suspension of 3.04 g (0.08 mol) lithium aluminium hydride in 80 mL anhydrous ether. The mixture was refluxed for 10 hours, then cooled. To the mixture, proper amount of 40% aqueous sodium hydroxide was added dropwise and the upper layer of ether was carefully poured out. The lower layer of solid was then washed with ether (×3). The resulting washing and extract ether were combined, dried over anhydrous potassium carbonate and filtered. To the filtrate, HCl-Et$_2$O was added under cooling until the solution is acidic. The solid was collected by filtering and recrystallized three times from iso-propanol and acetone to give a white lamellar crystal 3.33 g (yield 46.33%), mp 183-185° C. Elemental analysis for C$_9$H$_{22}$NCl (%): Calculated C, 10.15; H, 12.34; N, 7.79. Found C, 60.20; H, 13.80; N, 7.85. $^1$H-NMR(D$_2$O, ppm) 0.98(d, 6H), 1.00(t, 3H), 1.24(s, 6H), 1.63(m, 2H), 2.05(m, 1H), 2.98(t, 2H). MS(m/z) 143(M$^+$).

Example 3

Preparation of N-(1-methylpropyl)-2,3-dimethyl-2-butylamine (compound 13)

Similar treatment of 2,3-dimethyl-2-butylamine with bromoisobutane as example 1 gave compound 13 with a yield of 17.1%. The melting point (mp) of the hydrochloride is 203-204° C. Element analysis for C$_{10}$H$_{14}$NCl (%): Calculated C,61.99; H,12.49; N7.23. found C,62.17; H,13.18; N,7.27. MS (m/z) 157(M$^+$); $^1$H-NMR(D$_2$O, ppm) 0.90 (d, 6H), 1.18 (t, 3H), 1.26(d, 3H), 1.28-3.43(m, 19H).

Example 4

Preparation of N-cyclopropylmethyl-2,3-dimethyl-2-butylamine (compound 15)

Similar treatment of 2,3-dimethyl-2-butylamine with bromomethylcyclopropane as example 1 gave compound 15 with a yield of 27.6%. The melting point (mp) of hydrochloride is 176-178° C. Elemental analysis for C$_{10}$H$_{11}$NCl (%): Calculated C, 62.64; H, 11.57; N, 7.31. Found C, 62.69; H, 11.82; N, 7.01. $^1$H-NMR(D$_2$O, ppm) 0.95(d, 6H), 1.30-3.10 (m, 14H), 5.20(m, 1H). MS(m/z) 155(M$^+$), 112(M$^+$-43).

Example 5

Preparation of N-allyl-2,3-dimethyl-2-butylamine (compound 25)

Similar treatment of 2,3-dimethyl-2-butylamine with allylbromide as example 1 gave compound 25 with a yield of 79.3%. The melting point (mp) of the hydrochloride is 173-175° C. Elemental analysis for C$_9$H$_{20}$NCl (%): Calculated C, 60.80; H, 11.34; N, 7.88. Found C, 60.68; H, 11.43; N, 7.94. $^1$H-NMR(D$_2$O) 0.98(d, 6H), 1.31(s, 6H), 2.20(m, 1H), 3.66 (d, 2H), 5.87(m, 2H), 5.95(m, 1H). MS(m/z) 141(M$^+$).

Example 6

Preparation of N-{2-[di-(1-methylethyl)amino]ethyl}-2,3-dimethyl-2-butylamine (compound, 27)

Similar treatment of 2,3-dimethyl-2-butylamine with 2-(diisopropylamine)-ethylbromide as example 1 gave compound 27 with a yield of 31.8%. The melting point (mp) of the hydrochloride is 176-178° C. Elemental analysis for $C_{14}H_{34}N_2Cl_2$ (%): Calculated C, 55.80; H, 11.37; N, 9.30.; Found C, 55.90; H, 11.68; N, 9.21. $^1$H-NMR($D_2O$, ppm) 1.01(d, 6H), 1.38(s, 6H), 1.40(d, 12H), 2.04(m, 1H), 3.39-3.83(m, 6H). MS(m/z) 229($M^+$).

Example 7

Preparation of N-butyl-2,3-dimehyl-2-butylamine (compound 6).

According to the method of example 2, the Ritter reaction of butyronitrile and 2,3-dimethyl-2-butanol produced an amide intermediate, which was then reduced by lithium aluminium hydride to give compound 6 with a yield of 26.1%. The melting point (mp) of the hydrochloride is 140-142° C. Elemental analysis for $C_{10}H_{24}NCl$ (%): Calculated C,61.99; H,12.49; N,7.23. Found C, 62.06; H,12.73; N,5.90. MS(m/z) 157(M+). $^1$H-NMR($D_2O$, ppm) 0.98(d, 6H), 1.42(s, 6H), 1.45(t, 3H), 1.65(m 6H), 2.31(m, 1H).

Example 8

Preparation of N-propyl-α-methyl-phenylpropylamine (compound 21)

Similar treatment of propionitrile with 2-phenyl-2-butanol as example 2 gave compound 21. The melting point (mp) of the hydrochloride is 159-161° C. Elemental analysis for $C_{13}H_{22}NCl$ (%): Calculated C, 68.55; H, 9.73; N, 6.15. Found C, 68.59; H, 10.22; N, 5.86. $^1$H-NMR($D_2O$, ppm) 0.83(m, 6H, 2$CH_3$), 1.58(m, 2H, $CH_2$), 1.78(s, 3H, $CH_3$), 2.05(m, 1H, CH), 2.29(m, 1H, CH), 2.53(m, 1H, CH), 2.85 (m, 1H, CH), 7.54(m, 5H, Ar—H). MS(m/z) 192($M^+$), 133 ($M^+$-$C_3H_8N$).

Example 9

Preparation of N-propyl-α,β-dimethyl-phenylpropylamine (compound 19)

Similar treatment of propionitrile with 2-phenyl-3-methyl-2-butanol as example 2 gave compound 19. The melting point (mp) of the hydrochloride is 190-192° C. Elemental analysis for $C_{14}H_{24}NCl$ (%): Calculated C, 69.54; H, 10.00; N 5.79. Found C, 69.43; H, 10.40; N, 5.41. $^1$H—NMR($D_2O$, ppm) 0.98(t, 3H, $CH_3$), 1.28(s, 3H, $CH_3$), 1.39(t, 6H, 2$CH_3$), 1.63 (m, 2H, $CH_2$), 3.98(m, 1H, CH), 3.12-3.28(m, 2H, $CH_2$), 7.43(m, 5H, Ar—H). MS(m/z) 206($M^+$), 147($M^+$-$C_3H_8N$).

Example 10

Preparation of N-(3-pyridyl)methyl-2,3-dimethyl-2-butylamine (compound 39)

Similar treatment of 3-cyanopyridine with 2,3-dimethyl-2-butene as example 2 gave compound 39. The melting point (mp) of the hydrochloride is 166-168° C. , for $C_{12}H_{29}ClN_2O$ (%): Calculated C, 59.36; H, 7.89; N, 11.54. Found C, 59.33; H, 7.98; N, 11.45. $^1$H—NMR($D_2O$, ppm) 0.92(d, 6H, 2$CH_3$), 1.42(s, 6H, 2$CH_3$), 2.42(m, 1H, CH), 8.13(q, 1H, ArH), 8.86 (m, 2H, ArH), 9.08(s, 1H, ArH). MS(m/z) 207($M^+$), 106($M^+$-$C_6H_{14}N$).

Example 11

Preparation of N-valyl-2,3-dimethyl-2-butylamine (compound 37)

To a solution of 0.434 g (2 mmole) Boc-Val in 2.5 mL anhydrous tetrahydrofuran (THF), 0.200 g (2 mmole) 2,3-dimethyl-2-butylamine and 0.135 g (1 mmole) HOBt were added, while stirring untill the solid was completely dissolved. The mixture was cooled in an ice bath, and a solution of 0.412 g (2 mmol) DCC in 2.5 mL THF was added dropwise. The mixture was stirred for 4 h, then stood overnight and distilled off the solvent in vacuum to give a white solid. The solid was completely dissolved in 7.5 mL ethyl acetate, washed twice with saturated aqueous sodium bicarbonate, twice with saturated aqueous citric acid solution and twice with water in turn, then dried over anhydrous magnesium sulfate and filtered. The filtrate was washed twice with 7 ml ethyl acetate and 5 mL HCl-$Et_2O$ was added. After shaking, The mixture was stood for 5 hours at room temperature druing which shaking four times, then distilled off ether at room temperature, and distilled off ethyl acetate in vacuum in warm water bath to give a white laminar solid. 10 ml anhydious ether was added and stirred. The mixture was distilled in vacuum to remove ether. 0.324 g solid was obtained. The solid was recrystallized from anhydrous ethanol-ethyl acetate to give 0.165 g (yield 35%) product. The melting point of the hydrochloride is 240-241° C. Elemental analysis for $C_{11}H_{25}ClN_2O$ (%): Calculated C, 55.80; H, 10.64; N, 11.83. Found C. 55.85; H, 10.71; N, 11.63. MS(m/z) 201.0($M^+$).

Example 12

Preparation of N-tryptophanyl-2,3-dimethyl-2-butylamine (compound 40)

Similar treatment of Trp-Boc with 2,3-dimethyl-2-butylamine and DCC as example 11 gave compound 40 with a yield of 17.5%. The melting point (mp) of the hydrochloride is 135-137° C.(EtOH-EtAc-$Et_2O$). MS(m/z) 287($M^+$).

Example 13

Preparation of N-(N-nitroarginyl)-2,3-dimethyl-2-butylamine (compound 44)

Similar treatment of Boc-Arg($NO_2$) with 2,3-dimethyl-2-butylamine and DCC as example 11 gave compound 44 with a yield of 36.4%. The melting point (mp) of the hydrochloride is 175° C. (dec.)(EtOH-EtAc). MS(m/z): 302($M^+$).

Example 14

Preparation of N-phenylalanyl-2,3-dimethyl-2-butylamine (compound 43)

Similar treatment of Boc-Pha with 2,3-dimethyl-2-butylamine and DCC as example 11 gave compound 43 with a yield of 21.8%. The melting point (mp) of the hydrochloride is 232-233° C. (EtOH-$Et_2O$). MS(m/z) 248($M^+$).

Example 15

Preparation of N-leucyl-2,3-dimethyl-2-butylamine (compound 42)

Similar treatment of Boc-Leu with 2,3-dimethyl-2-butylamine and DCC as example 11 gave compound 42. The melting point (mp) of the hydrochloride is 250-252° C.(EtOH-$Et_2O$). MS(m/z) 214($M^+$).

Example 16

Preparation of N-isoleucyl-2,3-dimethyl-2-butylamine (compound 41)

Similar treatment of Boc-Ile with 2,3-dimethyl-2-butylamine and DCC as example 11 gave compound 41. The melting point (mp) of the hydrochloride is 246-248° C. (EtOH-Et$_2$O). MS(m/z) 214(M$^+$).

Example 17

Preparation of N-tosyl-2,3-dimethyl-2-butylamine (compound 38)

To a solution of 1.2 g (0.012 mole) 2,3-dimethyl-2-butylamine in 20 mL pyridine, a solution of 1.9 g (0.010 mole) tosylchloride in 20 mL pyridine was added dropwise in a glacial water bath, stirred for 3 hours in that bath and 1 hour at room temperature, then heated for 2 hours in a bath at temperature of 95-100° C. The solvent was distilled off in vacuum. Toluene was added to the residue, then distilled off the solvent in vacuum. The residue was dissolved in water and extracted with toluene (×4). The toluene extract was washed with water once, dried over anhydrous magnesium sulfate and filtered. The filtrate was distilled off the solvent. The residue was recrystallized from isopropanol to give a colorless columnar crystal 1.1 g, mp 80-89° C., recrystallized from isopropanol once again to give a white crystal 0.8 g, mp 88-89° C. Elemental analysis for C$_{13}$H$_{21}$NO$_2$S (%): Calculated C, 61.14; H, 8.29; N, 5.48. Found C, 61.11;, H, 8.37;, N, 5.55. $^1$H-NMR(CDCl$_3$; ppm) 0.91(d, J=6.8 Hz, 6H, 2CH$_3$), 1.17(s, 6H, 2CH$_3$), 1.82(M, 1H, CH), 2.47(s, 3H, CH$_3$), 7.32 (d,J=8.0, 2H,2Ar—H), 7.82(d, J=8.0, 2H, 2Ar—H'). MS(M/z) 255 (M$^+$), 172(B).

Example 18

Preparation of N-(1-methylethyl)-2,3-dimethyl-3-hydroxy-2-butylamine (compound 58)

To an autoclave, 41.8 g (0.418 mole) 2,3-dimethyl-2,3-epoxyethane, 20.0 g (0.33 mole) 2-propylamine and 50 mL toluene were added. The mixture was stirred for 48 h at 170° C., then cooled to room temperature and extracted with 6N aqueous hydrochloric acid (35 mL×3). The acid extract was combined and washed with proper amount of toluene, then adjusted to pH 12 with 40% aqueous sodium hydroxide and extraced with ether (50 mL×3). The ether extract was combined, dried over anhydrous potassium carbonate and filtered. The filtrate was distilled off ether, then distilled in vacuum to give 2-(N-2-methylethyl)-3-hydroxy-2,3-dimethylbutylamine, bp 60-65/10 mmHg. The melting point of the hydrochloride is 156-158° C. (EtOH-Et$_2$O). Elemental analysis for C$_9$H$_{22}$ClNO (%): ; C, 55.23; H, 11.33; N, 7.16. Found C, 55.23; H, 11.65; N, 6.95. $^1$H-NMR(CDCl$_3$, ppm) 1.33(s, 6H, 2CH$_3$), 1.41(d, 6H, 2CH$_3$), 1.42(s, 6H, 2CH$_3$), 3.81(m, 1H, CH). MS(m/z) 160 (M+).

Example 19

Preparation of N-(1-methylethyl)-2,3-dimethyl-2-butylamine tosylate

Anhydrous tosylic acid: Tosylic acid hydrate was heated to distill off crystal water at the temperature of 110° C. until no water vapored, then cooled in a desiccator for use in the next step.

0.60 g (3.5 mmole) anhydrous tosylic acid was dissolved in possibly as little as ethanol. Then a solution of 0.55 g (0.38 mmole) N-(1-methylethyl)-2,3-dimethyl-2-butylamine in 10 mL anhydrous ether was added dropwise with stirring. The mixture was stood overnight, and then distilled off the solvent. The residue was washed thoroughly with anhydrous ethanol to give a colorless solid 1.07 g, mp 119-120° C. $^1$H-NMR(D$_2$O, ppm) 0.96(d, 6H, 2CH$_3$), 1.303(s, 6H, 2CH$_3$), 1.36(d, 6H, 2CH$_3$), 2.02-2.15(m, 1H, C(H), 2.401(s, 3H, CH$_3$), 3.62-3.73(m, 1H, CH), 7.38(d,2H, 2Ar—H), 7.70 (d,2H, 2Ar—H).

Example 20

Preparation of N-(1-methylethyl)-2,3-dimethyl-2-butyl amine•hydrochloride

To a solution of 100.0 g N-(1-methylethyl)-2,3-dimethyl-2-butylamine in 200 mL ethanol, 100 mL hydrochloric acid was added with shaking and cooling in an glacial water bath. The solvent was distilled off to dry in vacuum. The residue was dissolve in ethanol, then distilled off to dry in vacuum and crystallized from 1:1 i-PrOH-c-Hex-H to give a solid 130.5 g (95.5%), mp 228-230° C.(i-PrOH:Et$_2$O). Elemental analysis for C$_9$H$_{22}$ClN(%): Calculated C, 60.14; H, 12.34; N, 7.79; Cl, 19.73. Found C, 60.14; H, 12.48; N, 7.31; Cl, 19.67. $^1$H-NMR (D$_2$O, ppm) 0.98(d, J=6.75H, 6H), 1.33(s, 6H), 1.37(d, J=6.46, 6H), 2.10(m, 1H), 3.70(m, 1H). MS(m/z) 143(M$^+$), 100(B).

Example 21

Preparation of N-(1-methylethyl)-N-(2,4,5-trichlorophenoxy-acetyl)-2,3-dimethyl-2-butylamine The mixture of 51.3 g 2,4,5-trichlorophenoxyacetic acid and 18 mL thionyl chloride was refluxed with: stirring for 2.5 hours. Then small quantity of dry benzene was added and distilled off excess thionyl chloride and benzene in vacuum. The residue was cooled and a white solid crystallized out, which is 2,4,5 trichlorophenoxyacetyl chloride.

To the mixture of 1.81 g N-(1-methylethyl)-2,3-dimethyl-2-butylamine•hydrochloride, 3.30 g triethylamine, catalytic amount of 4-dimethylaminopyridine and 50 mL toluene, a solution of 5.50 g 2,4,5-trichlorophenoxyacetyl chloride in 20 mL toluene was added dropwise with stirring. After addition, the mixture was heated for 14 hours in an oil bath at temperature of 80° C., then cooled to ambient temperature and filtered. The resulting solid was washed with toluene. The filtrate and the washing toluene were combined, washed with 50 mL water, 1N NaOH (50 mL×2), 50 mL water, 1N HCl (50 mL×2) and 50 mL water in turn, and dried over anhydrous sodium sulfate to give brown thick paste. The residue was purified by silica gel column chromatography to give 3.30 g (yield 86.8%) compound as a pale yellow semisolid. $^1$H-NMR(CDCl$_3$, ppm) 0.865(d, J=6.75 Hz, 6H), 1.401(s, 6H), 1.448(d, J=6.75 Hz, 6H), 2.85(m, 1H), 3.98(m, 1H), 4.740(s, 2H), 6.928(s, 1H), 7.441(s, 1H). MS (m/z) EI$^+$: 338/336(1:1, (M-i-Pr)$^+$), 298/296(M-thexyl)$^+$/294, 84(B, C$_6$H$_{12}$$^+$); FAB$^+$: 378.2/380.2(M+H)$^+$/382.2, 336.2/338.2(1: 1,(M-i-Pr)$^+$), 296.1/298.1(B, M+H—C$_6$H$_{12}$), 100.1 (t-hexylamine), 85.1(C$_6$H$_{13}$$^+$).

The following biological activity experiments are listed to explain the present invention.

Biological activity experiment 1. The effects of 16 compounds represented by formula I on blood pressure, heart rate, cardiac contraction and dilation in rats anesthetized with pentobarbital sodium.

TABLE 5

The structures and cardiovascular bioactivities of the
Compounds represented by formula I in the present invention

| compound | R$_1$ | R$_2$ | R$_3$ | R$_4$ | SBP | DBP | MBP | HR | LVSP | −dp/dtmax | Vpm |
|---|---|---|---|---|---|---|---|---|---|---|---|
| 2 | (CH$_3$)$_2$CH— | CH$_3$— | CH$_3$— | H— | 38 | 15 | 24 | 20 | 116 | 54 | 1.16 |
| 3 | (CH$_3$)$_2$CH— | CH$_3$— | CH$_3$— | CH$_3$— | 29 | 19 | 22 | 43 | 111 | 157 | 0.49 |

TABLE 5-continued

The structures and cardiovascular bioactivities of the
Compounds represented by formula I in the present invention

| compound | $R_1$ | $R_2$ | $R_3$ | $R_4$ | SBP | DBP | MBP | HR | LVSP | -dp/dtmax | Vpm |
|---|---|---|---|---|---|---|---|---|---|---|---|
| 4 | $(CH_3)_2CH-$ | $CH_3-$ | $CH_3-$ | $C_2H_5-$ | 31 | 23 | 25 | 44 | 146 | 177 | 0.45 |
| 5 | $(CH_3)_2CH-$ | $CH_3-$ | $CH_3-$ | $n-C_3H_7-$ | 34 | 25 | 28 | 78 | 162 | 187 | 0.58 |
| 6 | $(CH_3)_2CH-$ | $CH_3-$ | $CH_3-$ | $n-C_4H_9-$ | 61 | 43 | 49 | 111 | 263 | 276 | 0.98 |
| 7 | $(CH_3)_2CH-$ | $CH_3-$ | H— | $(CH_3)_2CH-$ | 34 | 34 | 34 | 46 | 184 | 226 | 1.08 |
| 8 | H— | H— | H— | $(CH_3)_2CH-$ | 28 | 24 | 26 | 53 | 121 | 124 | 1.45 |
| 9 | $C_2H_5-$ | $CH_3-$ | $CH_3-$ | $(CH_3)_2CH-$ | 50 | 36 | 40 | 108 | 260 | 245 | 1.68 |
| 10 | $C_2H_5-$ | $CH_3-$ | H— | H— | 2 | 5 | 4 | 20 | 21 | 27 | 0.25 |
| 11 | $C_2H_5-$ | $CH_3-$ | $CH_3-$ | $CH_3-$ | 18 | 10 | 13 | 19 | +159 | +86 | 0.1 |
| 12 | $C_2H_5-$ | $CH_3-$ | H— | H— | 25 | 23 | 24 | 39 | 112 | 129 | 0.58 |
| 40 | $(CH_3)_2CH-$ | $CH_3-$ | $CH_3-$ | Trp- | +2 | 0 | +0.7 | 6 | +23 | +6 | +0.1 |
| 41 | $(CH_3)_2CH-$ | $CH_3-$ | $CH_3-$ | Ile- | +2 | +1 | +1 | 16 | +4 | +2 | 0 |
| 42 | $(CH_3)_2CH-$ | $CH_3-$ | $CH_3-$ | Leu- | +2 | +2 | +2 | +1 | +10 | +13 | +0.18 |
| 43 | $(CH_3)_2CH-$ | $CH_3-$ | $CH_3-$ | Phe- | +3 | +1 | +2 | +10 | +31 | +10 | +0.13 |
| 44 | $(CH_3)_2CH-$ | $CH_3-$ | $CH_3-$ | $O_2N$-Arg- | +5 | +6 | +5.7 | 3 | +6 | +6 | +0.07 |

Notes:
The compounds were injected through femoral vein.
Doses (mg/kg): $1^\#(0.5)$, $2^\#(10)$, $3^\#(5)$, $4^\#(5)$, $5^\#(5)$, $6^\#(5)$, $7^\#(5)$, $8^\#(10)$, $9^\#(5)$, $10^\#(5)$, $11^\#(5)$, $12^\#(10)$, $40^\#(5)$, $41^\#(5)$, $42^\#(5)$, $43^\#(5)$, $44^\#(5)$.
SBP: systolic blood pressure;
DBP: diastolic blood pressure;
MBP: mean blood pressure;
HR: heart rate;
LVSP: left ventricular systolic pressure;
$-dp/dt_{max}$: the maximal rate of the decrease of left ventricular pressure;
Vpm: the physiological velocity of contractile element shorting. Data were expressed as mean, n = 3~5.
"+" means the increase after administration and all others mean decrease after administration.

It was suggested that compounds 2~12 could lower blood pressure or decrease heart rates, and inhibit cardiac contraction and dilation. It is reasonable to suggest that these compounds can be used in the managements for hypertension, blood pressure, tachycardia, angina pectoris and myocardial ischemic diseases. The compounds 40~44 could increase blood pressure and heart rates and improve cardiac contraction and dilation. It is also reasonable to suggest that these compounds can be used to higher blood pressure and in the managements for shock, bradycardia and congestive heart failure.

The methods of biological activity experiment 1 were as follows: Male Wistar rats, weighing 280±30 g were purchased from the experimental animal center of Academy of Military Medical Sciences. Rats were anesthetized with pentobarbital sodium (45 mg/kg) by peritoneal injection. A $PE_{50}$ polyethylene catheter was inserted into the left ventricle through right carotid artery for cardiac function measurement with a pressure energe exchanger, wherein the signal is put into a SMUP-PC biosignal processing system. Cardiac functional parameters such as HR, LVSP, $+dp/dt_{max}$, $-dp/dt_{max}$ and Vpm were recorded. Another two $PE_{50}$ polyethylene catheters were inserted into the right femoral artery and vein respectively for blood pressure measurement wherein the artery cathether was linked to a four-channel physiology recorder (RM-6000) through a MPU-0.5A Type pressure energe exchanger, which recorded SBP, DBP and MBP, while the vein catheter was used for compound administration. The methods were described by Liu Wei et al: Liu Wei, Wang Hai, Xiao Wen-Bin. Effects of pinacidil and nifedipine on cardiac functions in rats. Bull Acad Mil Med Sci 1996;20(4):245~248.

Biological activity experiment 2. The acute antihypertensive effects of compound 1 in conscious spontaneously hypertensive rats.

TABLE 6

The effects of compound 1 on systolic blood pressure in spontaneously hypertensive rats.

| drugs and dose | SBP | SBP (mmHg) at different time points (h) after administration | | | | | |
|---|---|---|---|---|---|---|---|
| (mg/kg po) | base value | 1 | 3 | 5 | 9 | 12 | 24 |
| control | | 239 ± 11 | 239 ± 14 | 238 ± 14 | 240 ± 9 | 242 ± 9 | 243 ± 12 | 245 ± 11 |
| compound 1 | 3 | 246 ± 11 | 227 ± 12*** | 218 ± 7*** | 215 ± 15*** | 229 ± 8* | 243 ± 7 | 244 ± 9 |
| pinacidil | 3 | 242 ± 5 | 208 ± 5*** | 236 ± 5* | 241 ± 4 | 242 ± 5 | 244 ± 5 | 244 ± 5 |
| nifedipine | 10 | 242 ± 5 | 186 ± 6*** | 219 ± 12* | 235 ± 5 | 240 ± 6 | 242 ± 4 | 242 ± 4 |
| bisoprolol | 60 | 242 ± 5 | 211 ± 7*** | 240 ± 7 | 242 ± 4 | 242 ± 3 | 243 ± 3 | 242 ± 6 |
| captopril | 40 | 243 ± 4 | 207 ± 9*** | 213 ± 11** | 233 ± 10* | 242 ± 4 | 241 ± 5 | 243 ± 4 |

Data were expressed as means ± SD for 9-13 rats.
*p < 0.05,
**p < 0.01,
***p < 0.001 vs control, using self-control t text.

TABLE 7

The effects of compound 1 on heart rates in spontaneously hypertensive rats.

| (mg/kg po) | | base value | 1 | 3 | 5 | 9 | 12 | 24 |
|---|---|---|---|---|---|---|---|---|
| control | | 402 ± 34 | 405 ± 31 | 419 ± 15 | 388 ± 30 | 393 ± 26 | 404 ± 32 | 395 ± 26 |
| compound 1 | 3 | 419 ± 20 | 414 ± 27 | 412 ± 27 | 408 ± 25 | 407 ± 21 | 413 ± 15 | 417 ± 12 |
| pinacidil | 3 | 351 ± 19 | 421 ± 17*** | 400 ± 15** | 354 ± 14 | 365 ± 16 | 352 ± 20 | 365 ± 15 |
| nifedipine | 10 | 352 ± 19 | 410 ± 11*** | 410 ± 31*** | 367 ± 24 | 365 ± 13 | 365 ± 16 | 364 ± 22 |
| bisoprolol | 60 | 355 ± 17 | 283 ± 17*** | 278 ± 16*** | 335 ± 34 | 320 ± 36 | 341 ± 28 | 360 ± 7 |
| captopril | 40 | 350 ± 17 | 380 ± 12*** | 370 ± 24* | 366 ± 22* | 355 ± 12 | 355 ± 29 | 364 ± 12 |

Data were expressed as means ± SD for 9-13 rats.
*$p < 0.05$,
**$p < 0.01$,
***$p < 0.001$ vs control, using self-control t test.

The results suggested that oral administration of compound 1 could induce antihypertensive actions. The duration of antihypertensive action lasted 9 hours. At the equivalent doses for producing the same antihypertensive action, compound 1 had antihypertensive effects of longer duration and had fewer effects on heart rates, compared with ATP-sensitive potassium channel opener pinacidil, calcium antagonist nifedipine, β-blocker bisoprolol and angiotensin converting enzyme inhibitor captopril.

The methods of biological activity experiment 2 were described by Long Chao-Liang et al: Long Chao-Liang, Wang Hai, Xiao Wen-Bin. Effects of pinacidil on, hypertensive vascular remodeling. Chin J Pharmacol Toxicol 1997; 11(1):42-46.

Biological activity experiment 3: The antagonism of glibenclamide, a selective ATP-sensitive potassium channel blocker, on the cardiovascular effects of compound 1 of formula Ia in the present invention.

TABLE 8

The antagonism of glibenclamide on the cardiovascular effects of compound 1.

| parameters | Pinacidil (n = 8) | | Glibenclamide + Pinacidil (n = 6) | | Nifedipine (n = 5) | |
|---|---|---|---|---|---|---|
| | B | A | B | A | B | A |
| SB (mmHg) | 128 ± 5 | 91 ± 8** | 142 ± 7 | 137 ± 4 | 144 ± 7 | 104 ± 8*** |
| DBP (mmHg) | 92 ± 5 | 67 ± 6*** | 95 ± 4 | 94 ± 3 | 95 ± 8 | 62 ± 7*** |
| MBP (mmHg) | 104 ± 5 | 76 ± 7** | 110 ± 5 | 108 ± 3 | 111 ± 7 | 76 ± 8*** |
| HR (bpm) | 353 ± 17 | 317 ± 25* | 322 ± 14 | 303 ± 17 | 335 ± 14 | 296 ± 22 |
| LVSP (mmHg) | 124 ± 6 | 111 ± 9* | 127 ± 8 | 131 ± 5 | 131 ± 6 | 113 ± 7*** |
| +dp/dtmax (kPa/a) | 673 ± 28 | 571 ± 33* | 725 ± 66 | 766 ± 37 | 761 ± 38 | 626 ± 57** |
| −dp/dtmax (kPa/a) | 536 ± 42 | 447 ± 73 | 584 ± 70 | 602 ± 38 | 650 ± 26 | 470 ± 40*** |
| Vpm (/a) | 4.3 ± 0.5 | 4.1 ± 0.5 | 6.1 ± 02 | 6.6 ± 0.1 | 5.7 ± 0.1 | 4.2 ± 0.5 |

| parameters | Glibenclamide + nifedipine (n = 5) | | Compound 1 (n = 8) | | glibenclamide + compound 1 (n = 7) | |
|---|---|---|---|---|---|---|
| | B | A | B | A | B | A |
| SB (mmHg) | 136 ± 4 | 104 ± 3** | 134 ± 8 | 105 ± 10* | 140 ± 6 | 132 ± 7 |
| DBP (mmHg) | 95 ± 6 | 62 ± 4** | 98 ± 7 | 77 ± 9** | 115 ± 3 | 109 ± 4 |
| MBP (mmHg) | 108 ± 5 | 75 ± 3** | 110 ± 7 | 86 ± 9** | 123 ± 3 | 116 ± 5 |
| HR (bpm) | 308 ± 12 | 273 ± 16 | 394 ± 13 | 357 ± 18 | 368 ± 18 | 353 ± 21 |
| LVSP (mmHg) | 130 ± 10 | 115 ± 8** | 180 ± 10 | 133 ± 6 | 151 ± 6 | 139 ± 6 |
| +dp/dtmax (kPa/a) | 766 ± 73 | 649 ± 81* | 978 ± 54 | 672 ± 36*** | 803 ± 51 | 723 ± 51* |
| −dp/dtmax (kPa/a) | 631 ± 88 | 471 ± 44* | 819 ± 56 | 507 ± 39*** | 595 ± 43 | 541 ± 24 |
| Vpm (/a) | 6.4 ± 0.7 | 4.2 ± 1.0* | 3.3 ± 0.2 | 2.7 ± 03** | 6.1 ± 0.6 | 5.6 ± 0.5 |

B: Before administration;
A: after administration.
Pinacidil (1.0 mg/kg), nifedipine (1.0 mg/kg) and compound 1 (0.5 mg/kg) were administered by iv. Glibenclamide (20 mg/kg) was pretreatment for ten minutes by iv. The parameters in Table 8 were measured 30 min after administering pinacidil, 10 min after nifedipine and 15 min after compound 1 respectively.
Data were expressed as means ± SE. Statistical significance between before and after administration was assessed by self-control t test,
*$p < 0.05$,
**$p < 0.01$,
***$p < 0.001$.

The results suggested that the effects of compound 1 on blood pressure, heart rates and cardiac contraction and dilation could be antagonized by glibenclamide, a selective ATP-sensitive potassium channel blocker. Under the same experimental conditions, glibenclamide could aslo block the cardiovascular effects of pinacidil, but had no effects on calcium channel blocker nifedipine. So compound 1 was revealed to possess the pharmacological properties of ATP-sensitive potassium channel activators.

The methods of Biological activity experiment 3 were the same as those described in the biological activity experiment 1.

Biological activity experiment 4. Allosteric regulation of novel compounds on ATP-sensitive potassium channels in vascular smooth muscles.

suggested that compound. 1 had allosteric effects on the binding sites of the antagonists for ATP-sensitive potassium channels in vascular smooth muscles. So compound I had the same activity as pinacidil, but contrary to that of ATP. As shown in Table 10, compound 1 (100 μmol $L^{-1}$), glibenclamide (10 μmol $L^{-1}$), ATP (10 mmol $L^{-1}$), ADP (1 mmol $L^{-1}$) and Ade (1 mmol $L^{-1}$) all inhibited the kinetic process of the association of [$^3$H]P1075 binding with ATP-sensitive potassium channels, while UDP accelerated the kinetic association process. These results suggested that compound 1 also had allosteric effects on binding sites of the agonists for ATP-sensitive potassium channels in vascular smooth muscles. It was the same as that of glibenclamide, ATP, ADP and Ade, but contrary to that of UDP.

TABLE 9

Effects of compound 1 on the association and dissociation kinetics of [$^3$H]glibenclamide binding to ATP-sensitive potassium channels in vascular smooth muscles.

| drugs | concentration mol · $L^{-1}$ = M | Association kinetics (×$10^{-2}$ $nM^{-1}$ · $min^{-1}$) | | | Dissociation kinetics | |
|---|---|---|---|---|---|---|
| | | $k_{obs}$ | $k_1$ | $k_A$ | $k_2$ (×$10^2$ $nM^{-1}$ · $min^{-1}$) | $K_d$ (nM) |
| control | | 4.65 ± 0.37 | 1.31 ± 0.14 | 181.90 ± 46.90 | 0.72 ± 0.11 | 0.55 ± 0.14 |
| compound 1 | $10^{-4}$ | 2.90 ± 0.74* | 0.62 ± 0.25* | 61.04 ± 25.89* | 1.02 ± 0.14* | 1.64 ± 0.69* |
| pinacidil | $10^{-4}$ | 2.32 ± 0.67** | 0.39 ± 0.24** | 33.91 ± 22.43** | 1.15 ± 0.27* | 2.95 ± 0.95* |
| ATP | $10^{-2}$ | 7.69 ± 1.01** | 2.42 ± 0.34** | 590.2 ± 208.20** | 0.42 ± 0.14* | 0.17 ± 0.06* |
| ADP | $10^{-3}$ | 2.28 ± 0.70** | 0.45 ± 0.24** | 47.80 ± 25.70** | 0.94 ± 0.10* | 2.09 ± 1.12* |
| UDP | 5 × $10^{-3}$ | 4.26 ± 0.65 | 1.15 ± 0.23 | 143.50 ± 49.00 | 0.80 ± 0.22 | 0.70 ± 0.24 |
| Ade | $10^{-3}$ | 2.83 ± 0.35* | 0.55 ± 0.14* | 47.40 ± 14.70** | 1.17 ± 0.21* | 2.11 ± 0.65* |

Data were expressed as means ± SD, n = 4~10. Statistical significance of differences between data was assessed by ANOVA followed by Dunnet's test.
*p < 0.05,
**p < 0.01.

TABLE 10

Effects of compound 1 on the association kinetics of [$^3$H]P1075 binding to ATP-sensitive potassium channels in vascular smooth muscles.

| drugs | concentration (mol · $L^{-1}$ = M) | Association kinetics ($k_{obs}$, ×$10^{-2}$ $nM^{-1}$ · $min^{-1}$) |
|---|---|---|
| control | | 4.36 ± 0.45 |
| Compound 1 | $10^{-4}$ | 2.44 ± 0.80* |
| Glibencamide | $10^{-5}$ | 3.12 ± 0.17* |
| ATP | $10^{-2}$ | 2.85 ± 0.08* |
| ADP | $10^{-3}$ | 2.63 ± 0.48* |
| UDP | 5 × $10^{-5}$ | 5.53 ± 0.51* |
| GTP | $10^{-3}$ | 3.86 ± 0.19 |
| Ade | $10^{-3}$ | 3.07 ± 0.24* |

Data were expressed as means ± SD, n = 4~10.
*p < 0.05 vs control, statistical significance of differences between data was assessed by group t-test.

The binding sites of antagonists and agonists for sulfourea receptors of ATP-sensitive potassium channels in vascular smooth muscles were labeled with[$^3$H]glibenclamide and [$^3$H] P1075 respectively. As shown in Table 9, compound 1 (100 μmol $L^{-1}$), pinacidil (100 μmol $L^{-1}$), ADP (1 mmol $L^{-1}$) and Ade (1 mmol $L^{-1}$) could inhibit the association and accelerate the disassociation of [$^3$H]glibenclamide with ATP-sensitive potassium channels in vascular smooth muscles. ATP (10 mmol $L^{-1}$) could accelerate the kinetic process of the association and retard the kinetic process of the disassociation of [$^3$H]glibenclamide binding with ATP-sensitive potassium channels in vascular smooth muscles. These results To study the allosteric regulation of compound 1 on ATP-sensitive potassium channels in vascular smooth muscles, the radio-labeled-ligand was used in the biological activity experiment 4.

1. The allosteric regulation of compound 1 on the binding sites for the selective $K_{ATP}$ blocker glibenclamide in vascular smooth muscles was studied as follows: After decapitated, the male Wistar rat (340±20 g) was immediately incised open the thoracic cavity. The aorta was dissected and immersed in the 4° C. buffer containing 10 mM HEPES to wash off the blood, then carefully extirpated the fat, peripheral connective tissues and thrombus. The aorta was cut into about 3-5 mm arterial rings and the vascular endothelium was scraped off with wet tampon. The arterial rings were blotted, weighted and transferred into the tubes containing proper amount of ice colded physiological saline buffer. In the association kinetics experiment, the arterial circles in the tubes were incubated with, compound 1($10^{-4}$M), pinacidil($10^{-4}$M), ATP($10^{-2}$M), ADP ($10^{-3}$M), Ade($10^{-3}$M), ADP(5×$10^{-5}$M) and equal volume of buffer respectively for 10 min in 25° C. water bath, and then added [$^3$H]-glibenclamide(3 nM). At 5,10,15,20,30,60,90 and 120 min after incubation, 9 mL ice colded Tris buffer (50 mM) was added to terminate the reaction. After washing off the free and bound [$^3$H]-glibenclamide, the aorta was blotted, transferred to a scintillator, added 50 uL 30% $H_2O_2$ and reacted for 2 h at 80° C. After cooling, 2.5 mL ethyl glycol and 5 mL 1% B-BPD xylene were added in sequence, kept stationary for 8 h and measured under a scintillometer for cpm value. The resulting data were fit into a regression line with ln[$B_{EQ}/(B_{EQ}-B_t)$]vs.t and the parameters for association kinetics were obtained. In the disassociation kinetics experiments, the aorta treated as described above and [$^3$H]-glibenclamide were incubated for 60 min at 25° C., and then 30 uM glibenclamide was added. 0,5,15,30,60,90 and 120 min later, the cpm values for the complex of [$^3$H]-glibenclamide and $K_{ATP}$ were measured. The resulting data were fit into a regression line with ln($B/B_{EQ}$)]vs.t and the parameters for disassociation kinetics were obtained.

2. The allosteric regulation of compound 1 on the binding sites for the selective $K_{ATP}$ activator P1075 in vascular smooth muscles was studied with the method as described above, but some conditions should be changed as follows: the incubation temperature was 37° C. instead of 25° C.;P1075 was used instead of glibenclamide; In the association kinetics experiments, the time points for sampling were 5,10,15,20, 30,45,60 and 90 min, while in the disassociation kinetics experiments, that were 1,3,5,10,20,30,45 and 60 min.

Biological activity experiment 5. The effects of compound 1 on the specific binding of high selective activator [$^3$H]P1075 with ATP-sensitive potassium channels in vascular smooth muscles.

As shown in FIG. 1, endothelium-removed smooth muscle samples derived from rat aorta were incubated with non-labeled P1075 and [$^3$H] P1075 (5 nmol L$^{-1}$) for 90 minutes at 37° C. P1075 could inhibit the specific binding of [$^3$H]P1075 in a concentration-dependent manner, of which the IC$_{50}$ value was 9.1±1.3 nmol L$^{-1}$, and pKi value was 8.04±0.88. Under the same experimental conditions, pinacidil, compound 1 and glibenclamide also could inhibit the specific binding of [$^3$H] P1075 in a concentration-dependent manner. The IC$_{50}$ values were 199.5±43.6 nmol L$^{-1}$, 354.8±53.7 nmol L$^{-1}$ and 58.9±4.6 μmol L$^{-1}$ respectively and the pKi values were 6.70±0.36, 6.45±0.73 and 4.23±2.34 respectively. The competitive inhibition effects of compound 1 on the binding of [$^3$H] P1075 was 39 times weaker than that of P1075 and 1.8 times weaker than that of pinacidil, but was 166 times stronger than that of glibenclamide. Compound 1 could displace [$^3$H]P1075 in the specific binding with sulfourea receptor of vascular smooth muscles in a concentration-dependent manner. The affinity of compound 1 with the binding site for ATP-sensitive potassium channel opener was similar with that of pinacidil.

The method of biological, activity experiment 5 was carried out as follows: After the male Wistar rat (350±46 g) was decapitated, the aorta was dissected out and then immersed in the buffer containing 5 mM HEPES at 4° C., carefully extirpated the outer tissue, capillary vessel and blood. After that, the aorta was cut into about 5-7 mm arterial rings with wet weight 5-7 mg and the vascular endothelium was removed mechanically. After weighted, the arterial rings were transferred into the tubes containing buffer.

The different tubes were all added the aorta sample (5-7 mg) and [$^3$H]P1075(5 nM), then added different concentration of potassium channel blockers (glibenclamide), potassium channel opener (pinacidil and P1075), compound 1, non-labled P1075(50 uM) and HEPES buffer (5 mM) respectively, at last added buffer to 250 uL. The reaction mixture was stired and incubated for 90 min at 37° C., then measured cpm value.

The experimental protocol were described in details in the publication: Bray K M, Quast U. A specific binding site for K$^+$ channel openers in rat aorta. J Biol Chem, 1993; 267(17): 11689-92.

Biological activity experiments 6. The effects of novel compounds on potassium currents in isolated arterial vascular smooth muscle cells (SMCs).

TABLE 11

The chemical structures of the compounds and their effects on the outward potassium currents of rat tail arterial SMCs.

| Compound | R$_1$ | R$_2$ | R$_3$ | R$_4$ | Currents (nA) Control + Compound $\overline{X}$ ± SD n = 5 | |
|---|---|---|---|---|---|---|
| 1 | (CH$_3$)$_2$CH— | CH$_3$— | CH$_3$— | (CH$_3$)$_2$CH— | 0.41 ± 0.08 | 119.3 ± 10.9** |
| 2 | (CH$_3$)$_2$CH— | CH$_3$— | CH$_3$— | H— | 0.91 ± 0.49 | 1.01 ± 0.57 |
| 3 | (CH$_3$)$_2$CH— | CH$_3$— | CH$_3$— | CH$_3$— | 0.56 ± 0.31 | 0.60 ± 0.34 |
| 4 | (CH$_3$)$_2$CH— | CH$_3$— | CH$_3$— | C$_2$H$_5$— | 0.61 ± 0.12 | 0.69 ± 0.14** |
| 5 | (CH$_3$)$_2$CH— | CH$_3$— | CH$_3$— | CH$_3$CH$_2$CH$_2$— | 0.65 ± 0.30 | 0.67 ± 0.30 |
| 6 | (CH$_3$)$_2$CH— | CH$_3$— | CH$_3$— | n-C$_4$H$_9$— | 0.49 ± 0.23 | 1.18 ± 0.54* |
| 13 | (CH$_3$)$_2$CH— | CH$_3$— | CH$_3$— | (CH$_3$)$_2$CHCH$_2$— | 0.55 ± 0.34 | 0.85 ± 0.31** |
| 15 | (CH$_3$)$_2$CH— | CH$_3$— | CH$_3$— | cyclopropyl-CH$_2$— | 0.83 ± 0.24 | 1.30 ± 0.45* |
| 24 | (CH$_3$)$_2$CH— | CH$_3$— | CH$_3$— | PhCH$_2$— | 0.65 ± 0.19 | 0.63 ± 0.19 |
| 25 | (CH$_3$)$_2$CH— | CH$_3$— | CH$_3$— | CH$_2$=CH—CH$_2$— | 0.68 ± 0.19 | 1.46 ± 0.50** |
| 39 | (CH$_3$)$_2$CH— | CH$_3$— | CH$_3$— | pyridyl-CO— | 0.46 ± 0.14 | 0.51 ± 0.22 |

The outward currents were, elicited in rat tail arterial SMCs by superfusing extracellular solution under whole cell recording configuration that the depolarizing pulse were applied from −30 mV to +100 mV with the holding potential of −40 mV in 100 ms, 10 mV clamp steps, a frequency of 5 KHz. The compounds were applied in the bath at the concentrations of 100 μmol L$^{-1}$. The amplitude of the outward potassium currents was recorded before and after compound application Values were expressed as means±SD. Statistical significance between two groups was evaluated by student's t-test for paired data * P<0.05 **P<0.01 vs control.

The results indicated that the compounds with different types of side chain R4 displayed differing abilities to promote potassium currents in terms of structure-activity relationships. These compounds with side chain R4 of isopropyl, ethyl, butyl; 1-methylpropyl, cyclopropylmethyl, allyl respectively, showed a powerful stimulation of potassium channel activities. Maximum potency was displayed by compound 25. While these compounds with side chain of hydrogen, methyl, propyl, benzyl, 2-pyridylformacyl respectively, displayed very slight activities, which were not statistically significant.

Figure 2:
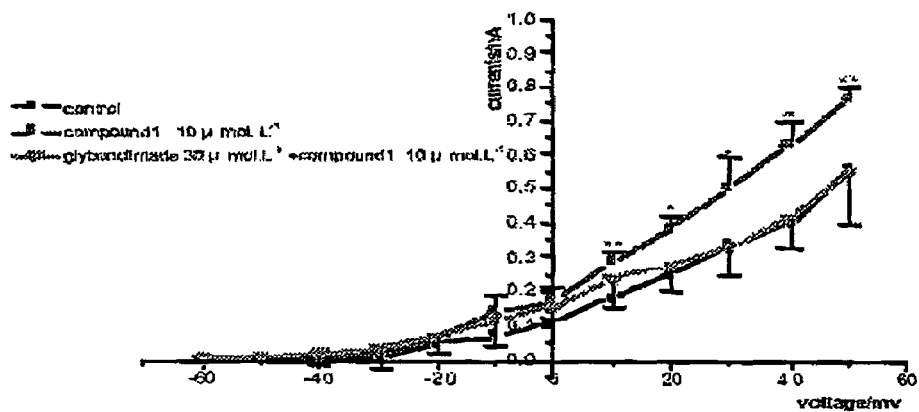
FIG. 2 shows the effects of compound 1 on potassium currents in artery smooth muscle cells derived from rats (n=8).

Effects of Compound 1 on Potassium Currents in Isolated Intrapulmonary arterial SMCs and Glibenclamide Antagonism The outward potassium currents were recorded in smooth muscle cells derived from intrapulmonary arteries of normotensive rats. Cells were sealed, clamped at −70 mV and depolarized to +50 mV at an increasing step of 10 mV with 100 ms duration. After application of compound 1 at the concentration of 10 μmol L$^{-1}$, the amplitude of the currents in 5/8 cells was increased to 115.4±2.8% compared with control recorded before compound application (P<0.01 n=5). While in the presence of both compound 1 and glibenclamide at the concentration of 10 μmol L$^{-1}$ and 30 μmol L$^{-1}$ respectively, the amplitude of the outward potassium currents in 7/7 cells was detected to be 83.1±8.3% of control, which was decreased compared with the presence of compound 1 only (P<0.01 n=7). The corresponding potassium current-voltage curves (I-V curves) were showed in FIG. 2.

These results suggested that the conpound 1 could enhance the outward potassium currents but these effects could be antagonized by glibenclamide, a specific blocker of adenosine triphosphate (ATP)-sensitive potassium channels. So it could be said that compound 1 possessed the pharmacological properties of ATP-sensitive potassium channel activators.

Method of Bioactive Experiment 6:

1. Preparation of single smooth muscle cells from rat tail arteries: Male Wistar rats (200-250 g) were killed by exsanguination. The tail artery was dissected out and transferred into cold physiological salt solution (PSS) of the following composition (in mM): NaCl 118.3, KCl 4.7, KH$_2$PO$_4$ 1.2, MgSO$_4$ 1.2, NaHCO$_3$ 25.0, CaCl$_2$ 2.5, EDTA 0.026 and Glucose 5.0 pH7.4. With the use of a dissecting microscope, the connective tissues were removed and the artery was cut open longitudinally. Endothelium was removed carefully with a cotton swab then the artery was cut into segments with 1 mm long and placed in 4° C. the extracellular solution containing (in mM) NaCl 130, KCl 5, MgCl$_2$ 1.2, HEPES 10, Glucose 10, pH7.2 for 20 min. After this incubation, the medium was changed to enzyme solution which was composed of collagenase I (1 mg ml$^{-1}$), papain (5 mg ml$^-$) and bovine serum albumin (2 mg ml$^{-1}$). The tissues, were incubated in this solution for 40 min, and then rinsed three times triturated using a fire-polished Pasteur pipette until the medium turned cloudily. The cell suspension was stored in the refrigerator at 4° C.

2. Preparation of smooth muscle cells from intrapulmonary arteries: Male Wistar rats were killed by decapitation. The intrapulmonary arteries were isolated and moved quickly into physiological salt solutions (PSS, 4° C.) Then the arteries were cut longitudinally and cut into small segments after scraping off the endothelium gently with a cotton swab. The fragments were then incubated at 37° C. in Ca$^{2+}$-free PSS for 20 to 30 minutes. This was followed by 58 minutes digestion at 37° C. in isolation solution containing: 2 mg ml$^{-1}$ bovine serum albumin, 1 mg ml$^{-1}$collagenase I 5 mg ml$^{-1}$papain, 1.25 mol L$^{-1}$ dithiothreitol and 16 μmol L$^{-1}$ Ca$^{2+}$. Next, the softened vessel segments were transferred to Ca$^{2+}$-free PSS and rinsed three times. The isolated single cells were gentle agitated with a polished glass pipette.

3. Whole cell recordings: A bath dish with the smooth muscle cells (SMCs) attached and superfused with the extracellular solution at a flow rate of 2 ml min$^{-1}$ was mounted onto the stage of an inverted-phase contrast microscope. The microelectrodes having a resistance of (5-8 MΩ) were made from borosilicate thin-wall glass capillaries, using an automatic multiple-stage, electronic puller (PP830 Japan) and then heat-polished. After establishing a high resistance seal, the patch membrane was disrupted by negative pressure. A commercial patch clamp amplifier (Axon 200B) was used to generate and apply voltages and sample current signals from the cell.

Figure 3:
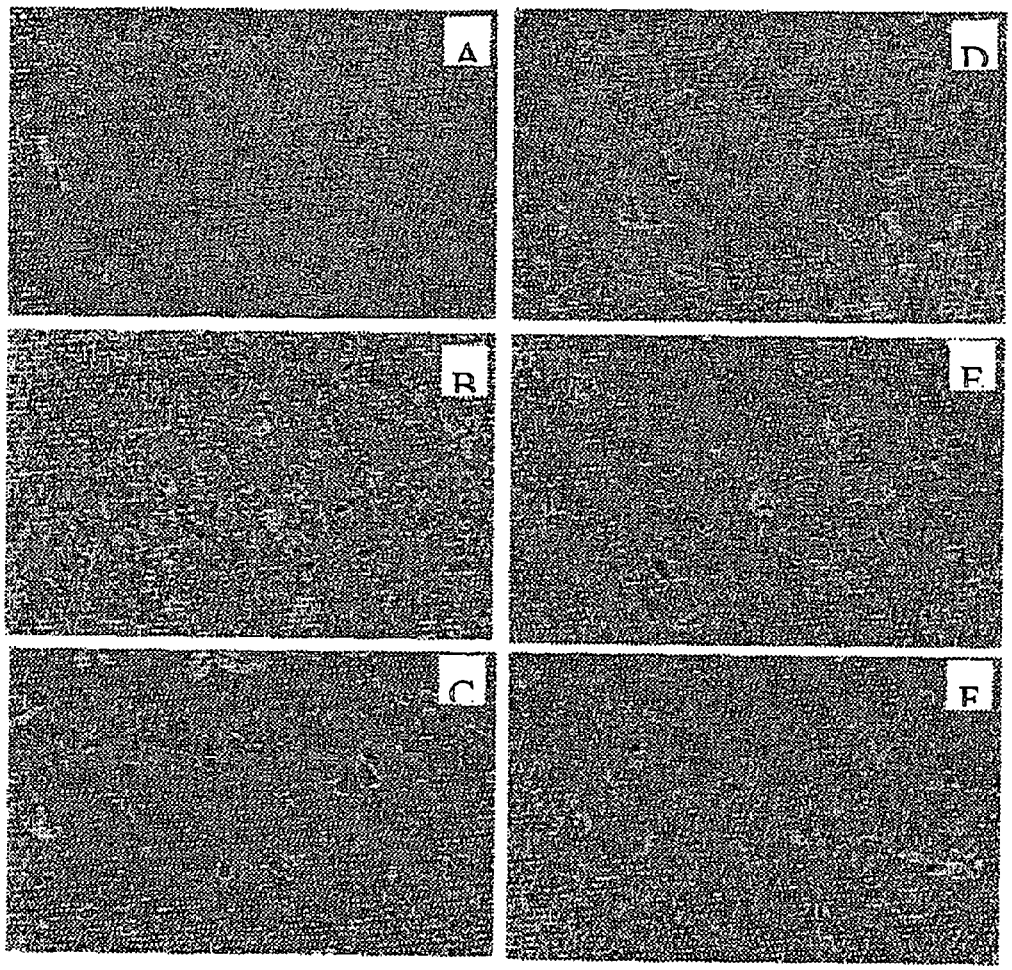
FIG. 3 shows the effects of compound 1 on potassium currents in artery smooth muscle cells derived from rats. X±SE, n=8, **P<0.01 over control.

Biological Activity Experiment 7 The Protective Effects of compound 1 on Pan-Cerebral Ischemia-Reperfusion Injury in Jirds As shown in FIG. 3, HE staining revealed that pan-cerebral ischemia decreased significantly the number of normal pyramidal nerve in hippocampal CA1 region of jirds. The mean number was only 15% of that of the control. Compound 1 could significantly decreased the number of dead pyramidal nerve of hippocampal CA1 region in jirds caused by pan-cerebral ischemia in a dosage-dependent manner (0.5-4.0 mg.kg$^{-1}$.d$^{-1}$;ip), and increase the number of normal pyramidal nerve. It suggested that compound 1 could significantly reverse ischmic nerve injure.

Figure 4:
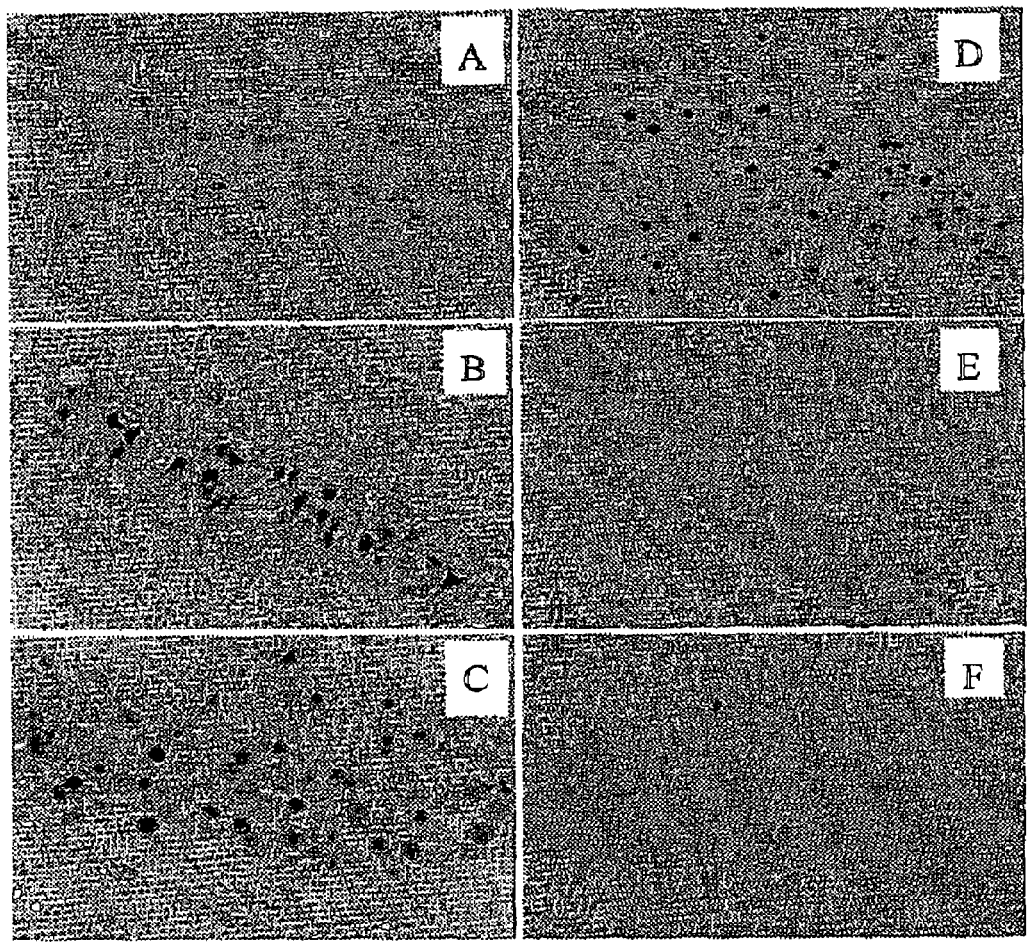
FIG. 4 shows the effects of compound 1 on the death of normal pyramidal nerve in hippocampal CA1 region of a jird caused by cerebral ischamia.

As shown in FIG. 4, enzyme-linked immunochemistry TUNEL revealed that in negative control group, the nucleus and cytoplasm of pyramidal nerve of hippocampal CA1 region in jirds were not stained, while in positive control group, the nucleus was stained, which confirmed the methods used in this study, were credible. Pan-cerebral ischemia greatly increased the number of apoptosized pyramidal nerve of hippocampal CA1 region in jirds, while compound 1 could significantly alleviate the apoptosis of pyramidal nerve of hippocampal CA1 region induced by pan-cerebral ischemia in a dosage-dependent manner. It suggested that compound 1 could significantly reverse ischemic nerve apoptosis.

The methods of biological activity experiment were carried out as follows: equal amounts of male and female jirds (60-70 g) were subjected to bilateral cervical aorta occlusion (BCAO) under narcotism. The drugs or equal amounts of physiological saline solution were injected peritoneally at 30 min before occlusion. After the blood flow in the bilateral cervical aorta was blocked for 5 min, reperfusion was restored and the drug was administered once a day for 7 days. During the BCAO, the body temperature was maintained at 37° C. In the control group, the cervical aorta was only exposed, while not blocked for blood flow. The animals were divided in 6 groups randomly: control group, ischemic group and compound-treated group (0.5, 1.0, 2.0 and 4.0 mg.kg$^{-1}$, ip). 7 days after BCAO, the animals were deeply anesthetized by injecting peritoneally 80 mg.kg$^{-1}$ pentobarbitol sodium, and perfused with 50 mL physiological saline solution and 4% paraformaldehyde through heart. The brain was dissected, immersed in 4% paraformaldehyde for 24 h, dehydrated, cleared, embedded with paraffin, sectioned and stained with HE. TUNEL staining was employed to detect the nerve apoptosis.

Biological activity experiment 8 the prophylaxis and treatment of cerebral apoplexy with compound 1 of formula I$_a$

TABLE 12

The effects of compound 1 on the rate and period needed for onset of SHR$_{sp}$ cerebral apoplexy

| group | n | Rate of cerebral apoplexy (%) | Period (d) |
|---|---|---|---|
| control | 12 | 83.3 | 48.3 ± 7.4 |
| Compound 1 (0.25 mg · kg$^{-1}$d$^{-1}$) | 12 | 72.7 | 58.6 ± 14.1* |
| Compound 1 (1 mg · kg$^{-1}$d$^{-1}$) | 12 | 40.0* | 60.8 ± 18.9* |
| Compound 1 (4 mg · kg$^{-1}$d$^{-1}$) | 12 | 33.3* | 68.6 ± 16.5** |
| Nimodipine (40 mg · kg$^{-1}$d$^{-1}$) | 12 | 36.4* | 66.0 ± 14.8** |

The data were expressed as means ± SD;
*p < 0.05,
**p < 0.01 vs control, group t-test.

Figure 5:
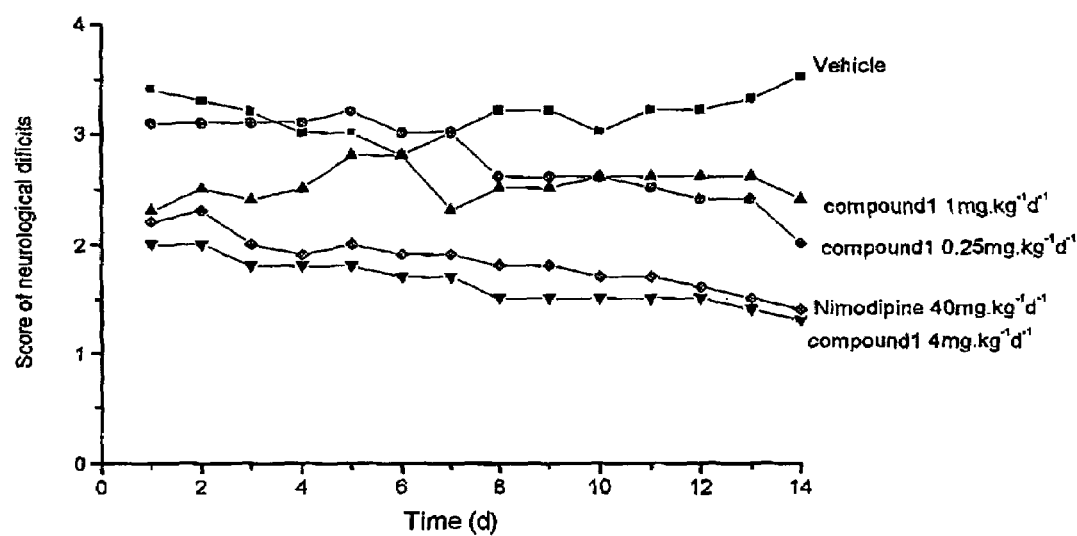
FIG. 5 shows the effects of compound 1 on the apoptosis of normal pyramidal nerve in hippocampal CA1 region of a jird caused by cerebral ischamia.

FIG. 5 The effects of compound 1 on grade value of nerve symptom of SHR$_{sp}$ cerebral apoplexy.

TABLE 13

The effects of compound 1 on death rate and survival time during SHR$_{sp}$ cerebral apoplexy

| group | n | Death rate of cerebral apoplexy (%) | Survival time (d) |
|---|---|---|---|
| control | 12 | 50.0 | 4.6 ± 3.8 |
| Compound 1 (0.25 mg · kg$^{-1}$d$^{-1}$) | 12 | 27.3 | 7.2 ± 5.3 |
| Compound 1 (1 mg · kg$^{-1}$d$^{-1}$) | 12 | 20.0 | 10.2 ± 4.1* |
| Compound 1 (4 mg · kg$^{-1}$d$^{-1}$) | 12 | 8.3* | 11.8 ± 3.2* |
| Nimodipine (40 mg · kg$^{-1}$d$^{-1}$) | 12 | 9.1* | 11.1 ± 2.7* |

The data were expressed as means ± SD;
*p < 0.05 vs control, group t-test.

The results showed that compound 1 and nimodipine could significantly decrease the rate of cerebral apoplexy and delay the onset of cerebral apoplexy, significantly improve the nerve symptom of cerebral apoplexy, and significantly lower the death rate of cerebral apoplexy and longer the animal's survival time.

The methods of biological activity experiments were carried out as follows: Desired concentration of compound 1 was prepared with distilled water, while desired concentration of nimodipine was prepared with market available Jinglongyu$^T$ oil. 30 male and 30 female SHR$_{sp}$ (10 weeks old, 120-180 g) were purchased from the vascular disease research center of Academy of Military Medical Science. All SHRsp were divided randomly into five groups based on blood pressure, body weight and sex: control group (fed with equal amount of Jinglongyu$^T$ oil), 0.25 mg.kg$^{-1}$d$^{-1}$ compound 1 treated group, 1.0 mg.kg$^{-1}$d$^{-1}$ compound 1 treated group, 4.0 mg.kg$^{-1}$d$^{-1}$ compound 1 treated group, and 4.0 mg.kg$^{-1}$d$^{-1}$ nimodipine treated group. Each group contained 12 animals and 4-5 animals were fed in a cage. The feedstaff (containing 23-24% protein) was purchased from experimental animal center of Academy of Military Medical Science. The animals were fed with tap water containing 1% NaCl to accelerate the onset of cerebral apoplexy. 12 normal WKY rats (with the same age and sex with the above) were selected as control, and fed with tap water and the same feedstuff. When reached 11 weeks old, the animals were fed with drugs for experiments.

Biological Activity Experiment 9 The Inhibition Effects of Compound 1 on the Cordical Nerve Apoptosis Induced by Low Level Oxygen and Glucose As shown in FIG. 6, the electron microscopy was used to observe the cordical nerve apoptosis induced by low level oxygen and glucose and the effects of compound 1 thereon. The chromatin distributed equably in normal cordical nerve cells and the cell membrane remained intact. However, in low level oxygen and glucose treated group, the cells were smaller, the chromatin was condensed, ruptured and distributed near the nuclear membrane, wherein some chromatin formed circle or crescent, and in late stage the cell membrane emboled and enwrapped the chromatin fragments to form apoptosis body. In 10 umol.L$^{-1}$ compound 1 treated group, the above mentioned changes were hardly observed. Moreover, the chromatin condensation decreased, and the nuclear membrane and cell membrane maintained intact. Therefore, the said concentration of compound 1 had the effects against the cordical nerve cell apoptosis induced by low level oxygen and glucose.

Figure 7:
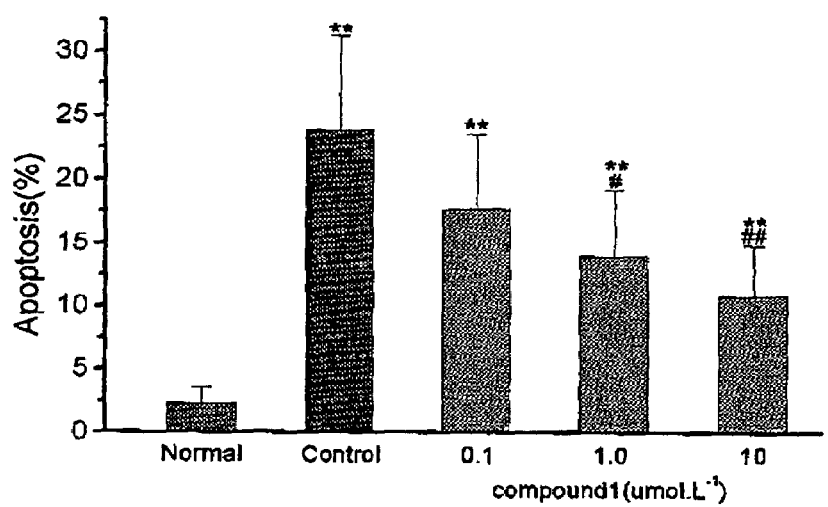
FIG. 7 shows the apoptosis of cordical nerve induced by low level of oxygen and glucose, and the effects of compound 1 (under the electronic microscopy).
Figure 8:
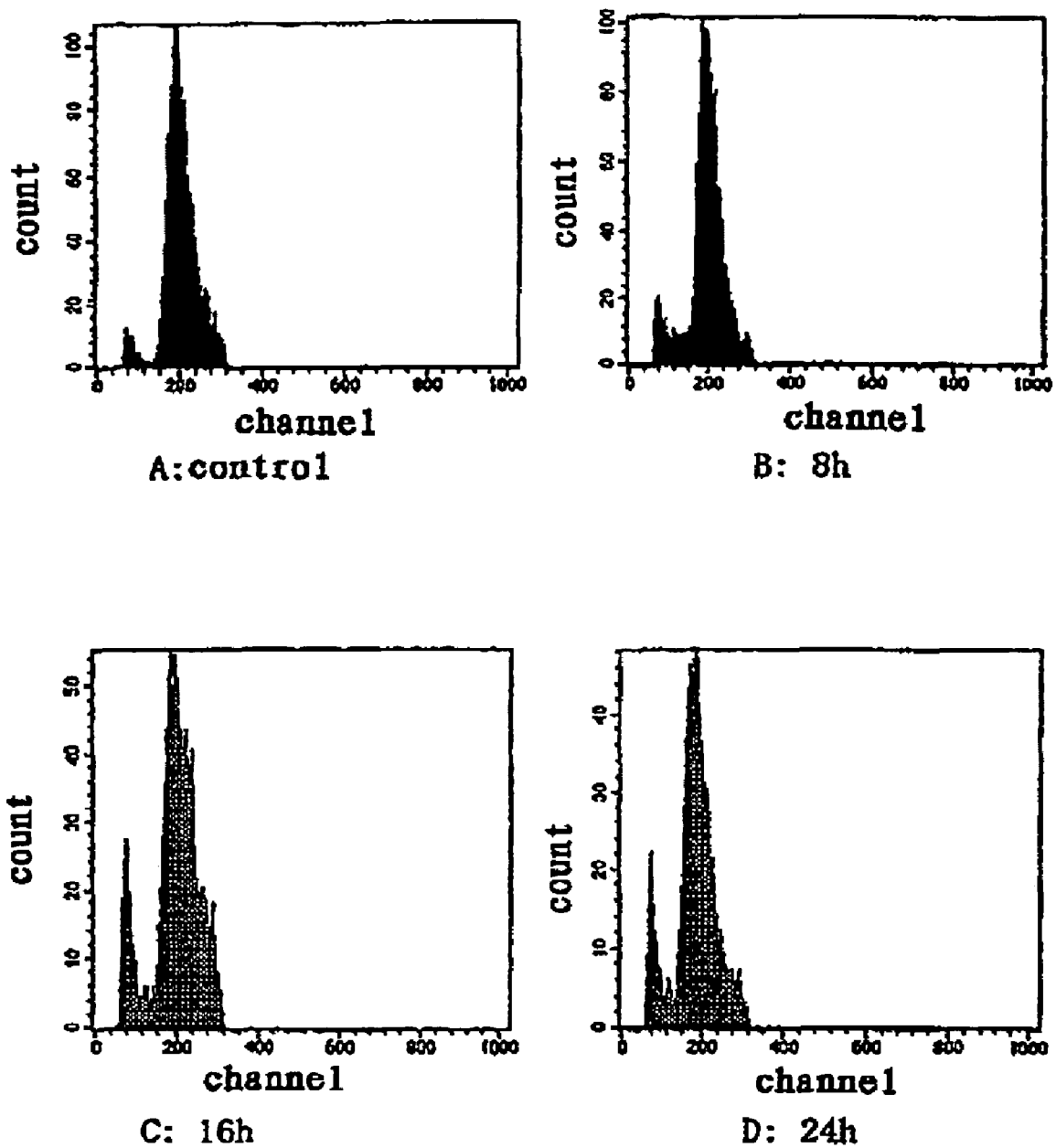
FIG. 8 shows the poptosis percentage of cordical nerve induced by low level of oxygen and glucose (under flow cytometr).

FIG. 7 showed the apoptosis percentage of cordical nerve induced by low level oxygen and glucose (under the flow cytometer). The cells were PI stained and the cells at different stages were measured for DNA content by the flow cytometer. In control group, most nerve cells were at $G_1$ stage and the apoptosis percentage was about 2.3%. In low level oxygen and glucose treated cells, $G_1$ sub-peak occurred at 8, 16 and 24 h, and the apoptosis percentage were 13.6±5.8%, 23.8±7.4% and 20.3±7.1%. The apoptosis was most significant at 16 h.

TABLE 14

The effects of compound 1 on the apoptosis percentage of cordical nerve induced by low level oxygen and glucose

| group | Apoptosis percentage (%) |
|---|---|
| Control | 2.3 ± 1.2 |
| Low level oxygen and glucose treated | 23.8 ± 7.4* |
| 0.1 umol · L$^{-1}$ compound 1 treated | 17.6 ± 5.8 |
| 1 umol · L$^{-1}$ compound 1 treated | 13.9 ± 5.2# |
| 10 umol · L$^{-1}$ compound 1 treated | 10.8 ± 4.1## |

The data were expressed as means ± SD;
*p < 0.01, vs control group;
p < 0.05,
p < 0.01, vs low level oxygen and glucose treated group.

The results showed that compound 1 could inhibit the cordical nerve apoptosis induced by low level oxygen and glucose in a dosage-dependent manner.

The methods of biological activity experiment 9 were carried out as follows: The cordical nerve were prepared from 12-hour old Wistar rats and cultured. See G. Y. Yang, A. L. Bentz. Reperfusion-induced injure to the blood-brain after middle cerebral artery occlusion in rats. Stroke, 1994,25: 1658-1665. Serum-free DMEM medium was applied 12 days later. The preparation was incubated in low oxygen tank (95% $N_2$+5% $CO_2$) for 8, 16 and 24 h respectively, and then restored oxygen to normal level for another 24 h. The experiments on five groups were as follows: the control group was cultured for 14 days with normal medium; low level oxygen and glucose treated group was cultured with normal medium for 12 days, then with serum-free medium containing low level oxygen and glucose for 16 h and with normal oxygen level for another 24 h; compound 1 treated group was cultured in serum-free medium containing low level oxygen and glucose for 16 h and with normal oxygen level for another 24 h, then added respectively different concentrations of compound 1 (0.1, 1.0 and 10 umol.L$^{-1}$). As to the method for detecting apoptosis by the electron microscopy and flow cytometer, refer to C.Du, R.Hu, C. A. Csernansky, et al. Very delayed infarction after mild focal cerebral ischemia: a role for apoptosis. J.Cereb.Flow Metab., 1996,16:195-201; M.Chopp, Y.Li, N.Jiang, et al. Antibodies against adhesion molecules reduced apoptosis after transient middle artery occlusion in rat brain. J.Cereb.Flow Metab., 1996,16:578-584.

What is claimed is:
1. An amine derivative represented by formula I$_a$,

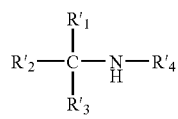

its racemes or optical isomers, its pharmaceutical acid addition salts or its amides or esters, wherein,
(1) when R'$_1$ is isopropyl and each of R'$_2$ and R'$_3$ represents methyl, R'$_4$ may be isopropyl, n-butyl, isobutyl, t-butyl, cyclopropylmethyl, allyl, dimethylaminoethyl, diisopropyl laminoethyl; or
(2) when each of R'$_1$ and R'$_2$ represents methyl, R'$_3$—C—NH—R'$_4$ may be an amine derivative represented by following formula
I'$_a$,

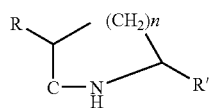

racemes or optical isomers thereof,
wherein each of R and R' represents C$_{1-5}$ hydrocarbyl, n represents an integer of one to eight; or
when R'$_1$ represents H$_2$NC(CH$_3$)$_2$—, and each of R'$_2$ and R'$_3$ represents methyl, R'$_4$ represents isopropyl;
or when R'$_1$ represents HOC(CH$_3$)$_2$—, and each of R'$_2$ and R'$_3$ represents methyl, R'$_4$ represents (CH$_3$)$_2$CH—or (CH$_3$)$_2$CH(CH$_3$)—;
or when R'$_1$ represents 1-hydroxylcyclohexyl, and each of R'$_2$ and R'$_3$ represents methyl, or R'$_2$ and R'$_3$ together represent —(CH$_2$)$_4$- or (CH$_2$)$_5$—, R'$_4$ represents (CH$_3$)$_2$CH—;
or when R'$_1$ represents O$_2$NOC(CH$_3$)$_2$—, and each of R'$_2$ and R'$_3$ represents methyl, R'$_4$ represents (CH$_3$)$_2$CH—;
or when R'$_1$ represents

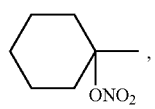

and each of R'$_2$ and R'$_3$ represents methyl, or R'$_2$ and R'$_3$ together represent —(CH$_2$)$_4$—or (CH$_2$)$_5$—, R'$_4$ represents (CH$_3$)$_2$CH—;

or when R'$_1$ represents

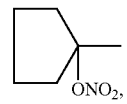

and each of R'$_2$ and R'$_3$ represents methyl, R'$_4$ represents (CH$_3$)$_2$CH—or (CH$_3$)$_2$CH(CH$_3$)—;
or when R'$_1$ represents

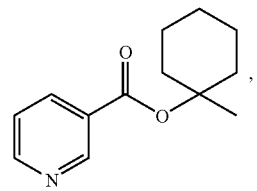

and each of R'$_2$ and R'$_3$ represents (CH$_2$)$_5$—, R'$_4$ represents (CH$_3$)$_2$CCH(CH$_3$)—; or
(4) when R'$_1$ represents cyclohexyl, and each of R'$_2$ and R'$_3$ represents methyl, R'$_4$ may represent

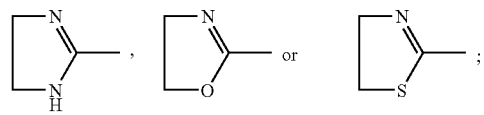

or
when R'$_1$ represents cyclopentyl, and R'$_2$ and R'$_3$ both represent —(CH$_2$)$_2$—, R'$_4$ may represent

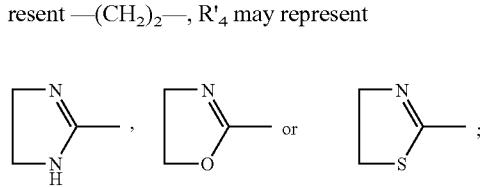

or
when R'$_1$ represents isopropyl, and each of R'$_2$ and R'$_3$ represents

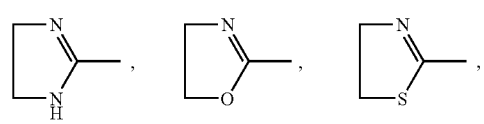

methyl, R'$_4$ may represent

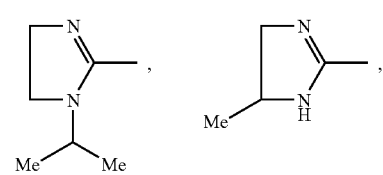

-continued

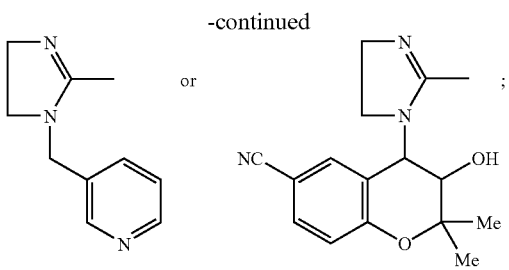

or
(5) when R'$_1$ represents isopropyl, and each of R'$_2$ and R'$_3$ represents methyl, R'$_4$ may represent Val-, Trp-, lle-, Leu-, Phe-, O$_2$N-Arg-, Pro-, Leu-Val-, Trp-Trp-Trp- or (CH$_3$)$_2$ CH—SO$_2$—; or R$_4$' may represent tosyl, nicotinyl, 4-chlorobenzoyl, morphorinoacetyl, 3-thienylacetyl, or 3-indotylacetyl; or when R'$_1$ represents cyclopropyl, and each of R'$_2$ and R'$_3$ represents —(CH$_2$)$_2$—, R'$_4$ represents Val-; or when R'$_1$ represents cyclohexyl, and each of R'$_2$ and R'$_3$ represents methyl, R'$_4$ represents Pro-; or when R'$_1$ represents cyclohexyl, and each of R'$_2$ and R'$_3$ represents —(CH$_2$)$_2$—, R'$_4$ represents Pro- or nicotinyl.

2. An amine derivative of claim 1, which may be selected from the group consisting of following compounds:
N-(1-methylethyl)-2,3-d imethyl-2-butylamine;
N-propyl-2,3-dimethyl-2-butylamine;
N-(2-methylpropyl)-2,3-dimethyl-2-butylamine;
N-cyclopropylmethyl-2,3-dimethyl-2-butylamine;
N-allyl-2,3-dimethyl-2-butylamine;
N-{2-[di-( 1-methylethyl)amino]ethyl}-2,3-dimethyl-2-butylamine;
N-butyl-2,3-dimethyl-2-butylamine;
N-propyl-α-methylphenylpropylamine;
N-propyl-α,β-dimethyl-phenylpropylamine;
N-(3-pyridyl)formyl-2,3-dimethyl-2-butylamine;
N-valyl-2,3-dimethyl-2-butylamine;
N-tryptophyl-2,3-dimethyl-2-butylamine;
N-(N-nitro)arginyl-2,3-dimethyl-2-butylamine;
N-phenylalanyl-2,3-dimethyl-2-butylamine;
N-leucyl-2,3-dimethyl-2-butylamine;
N-isoleucyl-2,3-dimethyl-2-butylamine;
N-tosyl-2,3-dimethyl-2-butylamine;
N-(1-methylethyl)-2,3-dimethyl-3-hydroxy-2-butylamine;
N-cinnamoyl-N-(1-methylethyl)-2,3-dimethyl-2-butylamine;
N-(1-methylethyl)-N-(2,4,5-trichlorophenoxyacetyl)-2,3-dimeth yl-2-butylamine.

3. The amine derivative of claim 1, wherein the pharmaceutical acid addition salts may be hydrochloride, sulfate, phosphate, hydrobromide; or acetate, oxalate, citrate, gluconate, succinate, tartarate, tosylate, methanesulfonate, benzoate, lactate or maleate.

4. The amine derivative of claim 1, wherein said compound is N-(1-methylethyl)-2,3-dimethyl-2-butylamine tosylate.

5. A method for preparation of an amine compound of formula I$_a$ as defined in claim 1, which includes the following steps: the solution of the primary amine R'$_1$R'$_2$R'$_3$CNH$_2$ and R'$_4$X in an organic solvent is heated to 50-300° C. and/or pressurized to 0.1-20 million pascal, wherein R'$_1$, R'$_2$, R'$_3$ and R'$_1$ are defined as in claim 1, X is a leaving group, characterized in that the primary amine R'$_1$ R'$_2$R'$_3$CNH$_2$ is produced by the following method:

(1) the mixture of urea, alcohol or alkene of R'$_1$R'$_2$R'$_3$C or a mixture of the both, and concentrated sulfuric acid is heated to 20-200° C. in the presence of an organic acid to yield the hydrocarbylurea R'$_1$R'$_2$R'$_3$C NHCONH$_2$; and
(2)-the hydrocarbylurea is hydrolyzed to give the corresponding primary amine, wherein said organic acid is selected from acetic acid, trifluoroacetic acid or methanesulfonic acid.

6. The method of claim 5, wherein the reaction of the primary amine with R'$_4$X is carried out in the presence of a catalyst, and the catalyst may be a deacidifying agent and/or a phase transfer catalyst.

7. The method of claim 6, wherein the deacidifying agent is a Lewis base, and the phase transfer catalyst is glycol or polyglycol.

8. The method of claim 5, wherein the organic solvent is toluene, xylene, 1,2-dichloroethane, 1,4-dioxane, dimethoxyethane, N,N-dimethylformide, N,N-dimethylacetamide, N-methylpyrrolidone, N,N-dimethylaniline, or N,N-diethylaniline.

9. A pharmaceutical composition, comprising at least an amine derivative represented by formula Ia or formula I, its racemes or optical isomers, its pharmaceutical acid addition salts or its amides or esters as claimed in any one of claims 1-4, and a pharmaceutical carrier or excipient.

* * * * *